(12) United States Patent
Lubock et al.

(10) Patent No.: US 9,415,239 B2
(45) Date of Patent: Aug. 16, 2016

(54) BRACHYTHERAPY DEVICE FOR FACILITATING ASYMMETRICAL IRRADIATION OF A BODY CAVITY

(75) Inventors: Paul Lubock, Laguna Niguel, CA (US); Michael L. Jones, San Clemente, CA (US); Frank R. Louw, Carlsbad, CA (US)

(73) Assignee: HOLOGIC, INC., Marlborough, MA (US)

( * ) Notice: Subject to any disclaimer, the term of this patent is extended or adjusted under 35 U.S.C. 154(b) by 1252 days.

(21) Appl. No.: 13/299,376

(22) Filed: Nov. 18, 2011

(65) Prior Publication Data

US 2012/0088952 A1    Apr. 12, 2012

Related U.S. Application Data

(63) Continuation of application No. 11/593,784, filed on Nov. 6, 2006, now Pat. No. 8,079,946, which is a continuation-in-part of application No. 11/283,236, filed on Nov. 18, 2005, now Pat. No. 7,413,539.

(60) Provisional application No. 60/819,919, filed on Jul. 11, 2006.

(51) Int. Cl.
*A61N 5/00* (2006.01)
*A61N 5/10* (2006.01)

(52) U.S. Cl.
CPC ....... *A61N 5/1015* (2013.01); *A61N 2005/1005* (2013.01); *A61N 2005/1018* (2013.01)

(58) Field of Classification Search
CPC . A61N 5/1001; A61N 5/1002; A61N 5/1007; A61N 5/1014
USPC ............................................. 600/1–8; 604/21
See application file for complete search history.

(56) References Cited

U.S. PATENT DOCUMENTS

| 3,324,847 A | 6/1967 | Zoumboulis |
| 3,502,878 A | 3/1970 | Stewart |
| 3,863,073 A | 1/1975 | Wagner |
| 3,872,856 A | 3/1975 | Clayton |
| 3,971,950 A | 7/1976 | Evans et al. |
| 3,975,350 A | 8/1976 | Hudgin et al. |

(Continued)

FOREIGN PATENT DOCUMENTS

| DE | 2539553 | 3/1977 |
| EP | 0340881 | 10/1992 |

(Continued)

OTHER PUBLICATIONS

*SenoRX, Inc.* v. *Hologic, Inc.*; District Court for the District of Delaware, Case No. 1:12-cv-00173-LPS-CJB, Complaint filed Feb. 10, 2012.

(Continued)

*Primary Examiner* — John Lacyk

(57) ABSTRACT

The disclosure describes devices and methods for asymmetrical irradiation at a body cavity or site, such as after removal of tissue, e.g. biopsy or cancer. One device includes a lumen which is off-set or off-settable from a longitudinal axis to increase the intensity of radiation received from a radiation source by a first tissue portion surrounding the body cavity and to reduce or minimize radiation received by a second tissue portion (e.g. healthy tissue) surrounding the body cavity.

23 Claims, 6 Drawing Sheets

(56) References Cited

U.S. PATENT DOCUMENTS

| | | |
|---|---|---|
| 4,119,094 A | 10/1978 | Micklus et al. |
| 4,160,906 A | 7/1979 | Daniels et al. |
| 4,310,766 A | 1/1982 | Finkenzeller et al. |
| 4,350,169 A | 9/1982 | Dutcher et al. |
| 4,417,576 A | 11/1983 | Baran |
| 4,454,106 A | 6/1984 | Gansow et al. |
| 4,496,557 A | 1/1985 | Malen et al. |
| 4,559,641 A | 12/1985 | Caugant et al. |
| 4,571,241 A | 2/1986 | Christopher |
| 4,690,677 A | 9/1987 | Erb |
| 4,706,269 A | 11/1987 | Reina et al. |
| 4,744,099 A | 5/1988 | Huettenrauch et al. |
| 4,754,745 A | 7/1988 | Horowitz |
| 4,763,642 A | 8/1988 | Horowitz |
| 4,773,086 A | 9/1988 | Fujita et al. |
| 4,773,087 A | 9/1988 | Plewes |
| 4,819,258 A | 4/1989 | Kleinman et al. |
| 4,821,725 A | 4/1989 | Azam et al. |
| 4,821,727 A | 4/1989 | Levene et al. |
| 4,867,741 A | 9/1989 | Portnoy |
| 4,929,470 A | 5/1990 | Rittenhouse et al. |
| 4,969,174 A | 11/1990 | Scheid et al. |
| 4,989,227 A | 1/1991 | Tirelli et al. |
| 4,998,917 A | 3/1991 | Geiser et al. |
| 4,998,930 A | 3/1991 | Lundahl |
| 5,015,247 A | 5/1991 | Michaelson |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,059,166 A | 10/1991 | Fischell et al. |
| 5,078,142 A | 1/1992 | Siczek et al. |
| 5,084,001 A | 1/1992 | Vant Hooft et al. |
| 5,084,015 A | 1/1992 | Moriuchi |
| 5,084,022 A | 1/1992 | Claude |
| 5,106,360 A | 4/1992 | Ishiwara et al. |
| 5,112,303 A | 5/1992 | Pudenz et al. |
| 5,152,747 A | 10/1992 | Olivier |
| 5,163,075 A | 11/1992 | Lubinsky et al. |
| 5,164,976 A | 11/1992 | Scheid et al. |
| 5,167,622 A | 12/1992 | Muto |
| 5,199,056 A | 3/1993 | Darrah |
| 5,199,939 A | 4/1993 | Dake et al. |
| 5,227,969 A | 7/1993 | Waggener et al. |
| 5,236,410 A | 8/1993 | Granov et al. |
| 5,240,011 A | 8/1993 | Assa |
| 5,259,847 A | 11/1993 | Trambert |
| 5,289,520 A | 2/1994 | Pellegrino et al. |
| 5,302,168 A | 4/1994 | Hess |
| 5,312,356 A | 5/1994 | Engelson et al. |
| 5,314,518 A | 5/1994 | Ito et al. |
| 5,336,178 A | 8/1994 | Kaplan et al. |
| 5,342,305 A | 8/1994 | Shonk |
| 5,359,637 A | 10/1994 | Webber |
| 5,365,562 A | 11/1994 | Toker |
| 5,381,504 A | 1/1995 | Novack et al. |
| 5,411,466 A | 5/1995 | Hess |
| 5,415,169 A | 5/1995 | Siczek et al. |
| 5,417,687 A | 5/1995 | Nardella et al. |
| 5,422,926 A | 6/1995 | Smith et al. |
| 5,426,685 A | 6/1995 | Pellegrino et al. |
| 5,428,658 A | 6/1995 | Oettinger et al. |
| 5,429,582 A | 7/1995 | Williams |
| 5,452,367 A | 9/1995 | Bick et al. |
| 5,484,384 A | 1/1996 | Fearnot |
| 5,503,613 A | 4/1996 | Weinberger |
| 5,506,877 A | 4/1996 | Niklason et al. |
| 5,520,646 A | 5/1996 | D'Andrea |
| 5,526,394 A | 6/1996 | Siczek et al. |
| 5,535,817 A | 7/1996 | Dunne |
| 5,539,797 A | 7/1996 | Heidsieck et al. |
| 5,553,111 A | 9/1996 | Moore et al. |
| 5,562,594 A | 10/1996 | Weeks |
| 5,566,221 A | 10/1996 | Smith et al. |
| 5,592,562 A | 1/1997 | Rooks |
| 5,594,769 A | 1/1997 | Pellegrino et al. |
| 5,596,200 A | 1/1997 | Sharma et al. |
| 5,598,454 A | 1/1997 | Franetzke et al. |
| 5,603,991 A | 2/1997 | Kupiecki et al. |
| 5,609,152 A | 3/1997 | Pellegrino et al. |
| 5,611,767 A | 3/1997 | Williams |
| 5,616,114 A | 4/1997 | Thorton et al. |
| 5,621,780 A | 4/1997 | Smith et al. |
| 5,624,395 A | 4/1997 | Mikhail et al. |
| 5,627,869 A | 5/1997 | Andrew et al. |
| 5,653,683 A | 8/1997 | D'Andrea |
| 5,657,362 A | 8/1997 | Giger et al. |
| 5,662,580 A | 9/1997 | Bradshaw et al. |
| 5,668,889 A | 9/1997 | Hara |
| 5,704,926 A | 1/1998 | Sutton |
| 5,706,327 A | 1/1998 | Adamkowski et al. |
| 5,719,952 A | 2/1998 | Rooks |
| 5,720,717 A † | 2/1998 | D'Andrea |
| 5,724,400 A | 3/1998 | Swerdloff et al. |
| 5,735,264 A | 4/1998 | Siczek et al. |
| 5,741,253 A | 4/1998 | Michaelson |
| 5,759,173 A | 6/1998 | Preissman et al. |
| 5,769,086 A | 6/1998 | Ritchart et al. |
| 5,782,742 A | 7/1998 | Crocker et al. |
| 5,800,333 A | 9/1998 | Liprie |
| 5,803,895 A | 9/1998 | Kronholz et al. |
| 5,803,912 A | 9/1998 | Siczek et al. |
| 5,818,898 A | 10/1998 | Tsukamoto et al. |
| 5,820,594 A | 10/1998 | Fontirroche et al. |
| 5,820,717 A | 10/1998 | Siegenthaler |
| 5,828,722 A | 10/1998 | Ploetz et al. |
| 5,851,182 A | 12/1998 | Sahadevan |
| 5,863,284 A | 1/1999 | Klein |
| 5,863,285 A | 1/1999 | Coletti |
| 5,872,828 A | 2/1999 | Niklason et al. |
| 5,878,104 A | 3/1999 | Ploetz |
| 5,896,437 A | 4/1999 | Ploetz |
| 5,899,882 A | 5/1999 | Waksman et al. |
| 5,908,406 A | 6/1999 | Ostapchenko et al. |
| 5,913,813 A | 6/1999 | Williams et al. |
| 5,916,143 A | 6/1999 | Apple et al. |
| 5,919,473 A | 7/1999 | Elkhoury |
| 5,924,973 A | 7/1999 | Weinberger |
| 5,931,774 A | 8/1999 | Williams et al. |
| 5,935,098 A | 8/1999 | Blaisdell et al. |
| 5,986,662 A | 11/1999 | Argiro et al. |
| 5,993,972 A | 11/1999 | Reich et al. |
| 6,005,907 A | 12/1999 | Ploetz |
| 6,022,308 A | 2/2000 | Williams |
| 6,022,325 A | 2/2000 | Siczek et al. |
| 6,033,357 A | 3/2000 | Ciezki et al. |
| 6,036,631 A | 3/2000 | McGrath et al. |
| 6,050,930 A | 4/2000 | Teirstein |
| 6,075,879 A | 6/2000 | Roehrig et al. |
| 6,083,148 A | 7/2000 | Williams |
| 6,086,970 A | 7/2000 | Ren |
| 6,091,841 A | 7/2000 | Rogers et al. |
| 6,093,142 A | 7/2000 | Ciamacco, Jr. |
| 6,095,966 A | 8/2000 | Chornenky et al. |
| 6,137,527 A | 10/2000 | Abdel-Malek et al. |
| 6,141,398 A | 10/2000 | He et al. |
| 6,143,013 A | 11/2000 | Samson et al. |
| 6,149,301 A | 11/2000 | Kautzer et al. |
| 6,175,117 B1 | 1/2001 | Komardin et al. |
| 6,196,715 B1 | 3/2001 | Nambu et al. |
| 6,200,257 B1 | 3/2001 | Winkler |
| 6,216,540 B1 | 4/2001 | Nelson et al. |
| 6,217,565 B1 | 4/2001 | Cohen |
| 6,219,059 B1 | 4/2001 | Argiro |
| 6,233,473 B1 | 5/2001 | Shepherd et al. |
| 6,234,952 B1 | 5/2001 | Liprie |
| 6,243,441 B1 | 6/2001 | Zur |
| 6,251,059 B1 | 6/2001 | Apple et al. |
| 6,256,370 B1 | 7/2001 | Yavuz |
| 6,256,529 B1 | 7/2001 | Holupka et al. |
| 6,267,775 B1 | 7/2001 | Clerc et al. |
| 6,272,207 B1 | 8/2001 | Tang |
| 6,282,142 B1 | 8/2001 | Miyawaki |
| 6,289,235 B1 | 9/2001 | Webber et al. |

(56) References Cited

U.S. PATENT DOCUMENTS

| | | |
|---|---|---|
| 6,292,530 B1 | 9/2001 | Yavus et al. |
| 6,306,074 B1 | 10/2001 | Waksman et al. |
| 6,319,188 B1 | 11/2001 | Lovoi |
| 6,327,336 B1 | 12/2001 | Gingold et al. |
| 6,341,156 B1 | 1/2002 | Baetz et al. |
| 6,375,352 B1 | 4/2002 | Hewes et al. |
| 6,378,137 B1 | 4/2002 | Hassan et al. |
| 6,390,967 B1 | 5/2002 | Forman et al. |
| 6,390,968 B1 | 5/2002 | Harmon |
| 6,390,992 B1 | 5/2002 | Morris et al. |
| 6,398,708 B1 | 6/2002 | Hastings et al. |
| 6,411,836 B1 | 6/2002 | Patel et al. |
| 6,413,203 B1 | 7/2002 | Sahatjian |
| 6,413,204 B1 | 7/2002 | Winkler et al. |
| 6,415,015 B2 | 7/2002 | Nicolas et al. |
| 6,416,457 B1 | 7/2002 | Urick et al. |
| 6,416,492 B1 | 7/2002 | Nielson |
| 6,442,288 B1 | 8/2002 | Haerer et al. |
| 6,458,069 B1 | 10/2002 | Tam et al. |
| 6,458,070 B1 | 10/2002 | Waksman et al. |
| 6,459,925 B1 | 10/2002 | Nields et al. |
| 6,482,142 B1 | 11/2002 | Winkler et al. |
| 6,501,819 B2 | 12/2002 | Unger et al. |
| 6,512,942 B1 | 1/2003 | Burdette et al. |
| 6,527,693 B2 | 3/2003 | Munro, III et al. |
| 6,540,655 B1 | 4/2003 | Chin et al. |
| 6,556,655 B1 | 4/2003 | Chichereau et al. |
| 6,558,390 B2 | 5/2003 | Cragg |
| 6,579,221 B1 | 6/2003 | Peterson |
| 6,597,762 B1 | 7/2003 | Ferrant et al. |
| 6,605,030 B2 | 8/2003 | Weinberger |
| 6,607,477 B1 | 8/2003 | Longton et al. |
| 6,610,013 B1 | 8/2003 | Fenster et al. |
| 6,611,575 B1 | 8/2003 | Alyassin et al. |
| 6,615,070 B2 | 9/2003 | Lee |
| 6,616,629 B1 | 9/2003 | Verin et al. |
| 6,620,111 B2 | 9/2003 | Stephens et al. |
| 6,626,849 B2 | 9/2003 | Huitema et al. |
| 6,633,674 B1 | 10/2003 | Barnes et al. |
| 6,638,235 B2 | 10/2003 | Miller et al. |
| 6,647,092 B2 | 11/2003 | Eberhard et al. |
| 6,673,006 B2 | 1/2004 | Winkler |
| 6,685,618 B2 | 2/2004 | Tam et al. |
| 6,706,014 B2 | 3/2004 | Banik et al. |
| 6,723,052 B2 | 4/2004 | Mills |
| 6,744,848 B2 | 6/2004 | Stanton et al. |
| 6,746,392 B2 | 6/2004 | Stiger et al. |
| 6,748,044 B2 | 6/2004 | Sabol et al. |
| 6,749,555 B1 | 6/2004 | Winkler et al. |
| 6,749,595 B1 | 6/2004 | Murphy |
| 6,751,285 B2 | 6/2004 | Eberhard et al. |
| 6,752,752 B2 | 6/2004 | Geitz |
| 6,758,824 B1 | 7/2004 | Miller et al. |
| 6,770,058 B1 | 8/2004 | Liprie |
| 6,813,334 B2 | 11/2004 | Koppe et al. |
| 6,882,700 B2 | 4/2005 | Wang et al. |
| 6,885,724 B2 | 4/2005 | Li et al. |
| 6,912,319 B1 | 6/2005 | Barnes et al. |
| 6,913,600 B2 | 7/2005 | Valley et al. |
| 6,923,754 B2 | 8/2005 | Lubock |
| 6,940,943 B2 | 9/2005 | Claus et al. |
| 6,955,641 B2 | 10/2005 | Lubock |
| 6,970,531 B2 | 11/2005 | Eberhard et al. |
| 6,978,040 B2 | 12/2005 | Berestov |
| 6,983,754 B1 | 1/2006 | Anderson et al. |
| 6,987,831 B2 | 1/2006 | Ning |
| 6,999,554 B2 | 2/2006 | Mertelmeier |
| 7,098,463 B2 | 8/2006 | Adamovics |
| 7,107,089 B2 | 9/2006 | Lee |
| 7,110,490 B2 | 9/2006 | Eberhard et al. |
| 7,110,502 B2 | 9/2006 | Tsuji |
| 7,123,684 B2 | 10/2006 | Jing et al. |
| 7,127,091 B2 | 10/2006 | Op De Beek et al. |
| 7,142,633 B2 | 11/2006 | Eberhard et al. |
| 7,171,255 B2 | 1/2007 | Holupka et al. |
| 7,201,715 B2 | 4/2007 | Burdette et al. |
| 7,214,178 B2 | 5/2007 | Lubock |
| 7,245,694 B2 | 7/2007 | Jing et al. |
| 7,315,607 B2 | 1/2008 | Ramsauer |
| 7,319,735 B2 | 1/2008 | Defreitas |
| 7,322,929 B2 | 1/2008 | Lovoi |
| 7,323,692 B2 | 1/2008 | Rowlands et al. |
| 7,404,791 B2 | 7/2008 | Linares et al. |
| 7,407,476 B2 | 8/2008 | Lubock et al. |
| 7,413,539 B2 | 8/2008 | Lubock et al. |
| 7,430,272 B2 | 9/2008 | Jing et al. |
| 7,443,949 B2 | 10/2008 | Defreitas et al. |
| 7,465,268 B2 | 12/2008 | Lubock et al. |
| 7,476,235 B2 | 1/2009 | Diederich et al. |
| 7,497,819 B2 | 3/2009 | White et al. |
| 7,497,820 B2 | 3/2009 | White et al. |
| 7,513,861 B2 | 4/2009 | Klein et al. |
| 7,517,310 B2 | 4/2009 | Lubock et al. |
| 7,609,806 B2 | 10/2009 | Defreitas et al. |
| 7,630,533 B2 | 12/2009 | Ruth et al. |
| 7,662,082 B2 | 2/2010 | White et al. |
| 7,697,660 B2 | 4/2010 | Ning |
| 7,783,006 B2 | 8/2010 | Stewart et al. |
| 7,792,245 B2 | 9/2010 | Hitzke et al. |
| 7,869,563 B2 | 1/2011 | Defreitas et al. |
| 7,885,382 B2 | 2/2011 | Stewart et al. |
| 7,887,476 B2 | 2/2011 | Hermann et al. |
| 8,075,469 B2 | 12/2011 | Lubock et al. |
| 8,079,946 B2 | 12/2011 | Lubock et al. |
| 8,137,256 B2 | 3/2012 | Cutrer et al. |
| 8,192,344 B2 | 6/2012 | Lubock et al. |
| 8,277,370 B2 | 10/2012 | Quick |
| 8,287,442 B2 | 10/2012 | Quick |
| 8,565,374 B2 | 10/2013 | Defreitas et al. |
| 9,180,312 B2 | 11/2015 | Lubock et al. |
| 9,248,311 B2 | 2/2016 | Damarati |
| 2001/0016725 A1 | 8/2001 | Valley et al. |
| 2001/0038681 A1 | 11/2001 | Stanton et al. |
| 2001/0038861 A1 | 11/2001 | Hsu et al. |
| 2001/0049464 A1 | 12/2001 | Ganz |
| 2001/0051669 A1 | 12/2001 | McGhee |
| 2002/0012450 A1 | 1/2002 | Tsujii |
| 2002/0026090 A1 | 2/2002 | Kaplan et al. |
| 2002/0045893 A1 | 4/2002 | Lane et al. |
| 2002/0050986 A1 | 5/2002 | Inoue et al. |
| 2002/0055666 A1 | 5/2002 | Hunter et al. |
| 2002/0075997 A1 | 6/2002 | Unger et al. |
| 2002/0095114 A1 | 7/2002 | Palasis |
| 2002/0156342 A1 | 10/2002 | Burton et al. |
| 2002/0177804 A1 | 11/2002 | Saab |
| 2003/0018272 A1 | 1/2003 | Treado et al. |
| 2003/0073895 A1 | 4/2003 | Nields et al. |
| 2003/0095624 A1 | 5/2003 | Eberhard |
| 2003/0144570 A1 | 7/2003 | Hunter et al. |
| 2003/0153803 A1 | 8/2003 | Harmon |
| 2003/0194050 A1 | 10/2003 | Eberhard |
| 2003/0194051 A1 | 10/2003 | Wang et al. |
| 2003/0194121 A1 | 10/2003 | Eberhard et al. |
| 2003/0210254 A1 | 11/2003 | Doan et al. |
| 2003/0215120 A1 | 11/2003 | Uppaluri et al. |
| 2004/0039437 A1 | 2/2004 | Sparer et al. |
| 2004/0054366 A1 | 3/2004 | Davison et al. |
| 2004/0066884 A1 | 4/2004 | Hermann Claus et al. |
| 2004/0066904 A1 | 4/2004 | Eberhard et al. |
| 2004/0087827 A1 | 5/2004 | Lubock |
| 2004/0094167 A1 | 5/2004 | Brady et al. |
| 2004/0101095 A1 | 5/2004 | Jing et al. |
| 2004/0109529 A1 | 6/2004 | Eberhard et al. |
| 2004/0116767 A1 | 6/2004 | Lebovic et al. |
| 2004/0147800 A1 | 7/2004 | Barber et al. |
| 2004/0171986 A1 | 9/2004 | Tremaglio, Jr. et al. |
| 2004/0215048 A1 | 10/2004 | Lubock |
| 2004/0260142 A1 | 12/2004 | Lovoi |
| 2004/0267157 A1 | 12/2004 | Miller et al. |
| 2005/0016771 A1 | 1/2005 | Mayes |
| 2005/0049521 A1 | 3/2005 | Miller et al. |
| 2005/0061771 A1 | 3/2005 | Murphy |
| 2005/0063509 A1 | 3/2005 | DeFreitas et al. |
| 2005/0078797 A1 | 4/2005 | Danielsson et al. |

(56) References Cited

U.S. PATENT DOCUMENTS

| | | |
|---|---|---|
| 2005/0080313 A1 | 4/2005 | Stewart et al. |
| 2005/0101823 A1 | 5/2005 | Linares et al. |
| 2005/0105679 A1 | 5/2005 | Wu et al. |
| 2005/0113681 A1 | 5/2005 | DeFreitas |
| 2005/0113715 A1 | 5/2005 | Schwindt et al. |
| 2005/0124843 A1 | 6/2005 | Singh |
| 2005/0129172 A1 | 6/2005 | Mertelmeier |
| 2005/0135555 A1 | 6/2005 | Claus et al. |
| 2005/0135664 A1 | 6/2005 | Kaufhold et al. |
| 2005/0182286 A1 | 8/2005 | Lubock |
| 2005/0226375 A1 | 10/2005 | Eberhard et al. |
| 2005/0240073 A1 | 10/2005 | Apffelstaedt et al. |
| 2005/0240074 A1 | 10/2005 | Lubock |
| 2005/0267320 A1 | 12/2005 | Barber et al. |
| 2005/0277577 A1 | 12/2005 | Hunter et al. |
| 2006/0014997 A1 | 1/2006 | Kindlein et al. |
| 2006/0020156 A1 | 1/2006 | Shukla |
| 2006/0020256 A1 | 1/2006 | Bell et al. |
| 2006/0030784 A1 | 2/2006 | Miller et al. |
| 2006/0074288 A1 | 4/2006 | Kelly |
| 2006/0098855 A1 | 5/2006 | Gkanatsios |
| 2006/0100475 A1 | 5/2006 | White et al. |
| 2006/0116546 A1 | 6/2006 | Eng |
| 2006/0129062 A1 | 6/2006 | Nicoson et al. |
| 2006/0136051 A1 | 6/2006 | Furst et al. |
| 2006/0149186 A1 | 7/2006 | Wantink |
| 2006/0155209 A1 | 7/2006 | Miller et al. |
| 2006/0167416 A1 | 7/2006 | Mathis et al. |
| 2006/0173233 A1 | 8/2006 | Lovoi |
| 2006/0173235 A1 | 8/2006 | Lim et al. |
| 2006/0205992 A1 | 9/2006 | Lubock et al. |
| 2006/0291618 A1 | 12/2006 | Eberhard et al. |
| 2007/0005003 A1 | 1/2007 | Patterson et al. |
| 2007/0030949 A1 | 2/2007 | Jing et al. |
| 2007/0036265 A1 | 2/2007 | Jing et al. |
| 2007/0055144 A1 | 3/2007 | Neustadter et al. |
| 2007/0076844 A1 | 4/2007 | Defreitas et al. |
| 2007/0106108 A1 | 5/2007 | Hermann et al. |
| 2007/0142694 A1 | 6/2007 | Cutrer et al. |
| 2007/0167665 A1 | 7/2007 | Hermann et al. |
| 2007/0167666 A1 | 7/2007 | Lubock et al. |
| 2007/0191667 A1 | 8/2007 | Lubock et al. |
| 2007/0223651 A1 | 9/2007 | Wagenaar et al. |
| 2007/0225600 A1 | 9/2007 | Weibrecht |
| 2007/0242800 A1 | 10/2007 | Jing |
| 2007/0270627 A1 | 11/2007 | Cutrer et al. |
| 2008/0009659 A1 | 1/2008 | Smith et al. |
| 2008/0019581 A1 | 1/2008 | Gkanatsios |
| 2008/0045833 A1 | 2/2008 | Defreitas |
| 2008/0057298 A1 | 3/2008 | Finley |
| 2008/0064915 A1 | 3/2008 | Lubock |
| 2008/0071212 A1 | 3/2008 | Lubock et al. |
| 2008/0086083 A1 | 4/2008 | Towler |
| 2008/0091055 A1 | 4/2008 | Nguyen et al. |
| 2008/0101537 A1 | 5/2008 | Sendai |
| 2008/0112534 A1 | 5/2008 | DeFreitas |
| 2008/0130979 A1 | 6/2008 | Ren |
| 2008/0177127 A1 | 7/2008 | Allan et al. |
| 2008/0188705 A1 | 8/2008 | Lubock et al. |
| 2008/0221384 A1 | 9/2008 | Chi Sing et al. |
| 2008/0221444 A1 | 9/2008 | Ritchie et al. |
| 2008/0228023 A1 | 9/2008 | Jones et al. |
| 2008/0228024 A1 | 9/2008 | Jones et al. |
| 2008/0228025 A1 | 9/2008 | Quick |
| 2008/0228150 A1 | 9/2008 | Jones et al. |
| 2008/0281142 A1 | 11/2008 | Lubock et al. |
| 2008/0281143 A1 | 11/2008 | Lubock et al. |
| 2008/0287801 A1 | 11/2008 | Magnin et al. |
| 2009/0003519 A1 | 1/2009 | Defreitas |
| 2009/0010384 A1 | 1/2009 | Jing |
| 2009/0030259 A1 | 1/2009 | Quick |
| 2009/0080594 A1 | 3/2009 | Brooks |
| 2009/0080602 A1 | 3/2009 | Brooks |
| 2009/0093821 A1 | 4/2009 | Edmundson |
| 2009/0124845 A1 | 5/2009 | Lubock et al. |
| 2009/0135997 A1 | 5/2009 | Defreitas |
| 2009/0156880 A1 | 6/2009 | Allan et al. |
| 2009/0156882 A1 | 6/2009 | Chi Sing et al. |
| 2009/0171157 A1 | 7/2009 | Diederich et al. |
| 2009/0188098 A1 | 7/2009 | Acosta et al. |
| 2009/0198095 A1 | 8/2009 | Acosta et al. |
| 2009/0213987 A1 | 8/2009 | Stein et al. |
| 2009/0268865 A1 | 10/2009 | Ren |
| 2009/0296882 A1 | 12/2009 | Gkanatsios |
| 2009/0304147 A1 | 12/2009 | Jing et al. |
| 2010/0048977 A1 | 2/2010 | Sing et al. |
| 2010/0054400 A1 | 3/2010 | Ren |
| 2010/0086188 A1 | 4/2010 | Ruth |
| 2010/0150306 A1 | 6/2010 | Defreitas et al. |
| 2010/0195882 A1 | 8/2010 | Ren |
| 2010/0204534 A1 | 8/2010 | Damarati |
| 2010/0226475 A1 | 9/2010 | Smith |
| 2010/0286465 A1 | 11/2010 | Benson |
| 2010/0290585 A1 | 11/2010 | Eliasson |
| 2011/0069809 A1 | 3/2011 | Defreitas et al. |
| 2012/0178983 A1 | 7/2012 | Benson |
| 2013/0225902 A1 † | 8/2013 | White |

FOREIGN PATENT DOCUMENTS

| | | |
|---|---|---|
| EP | 0536440 A1 | 4/1993 |
| EP | 0642766 A2 | 3/1995 |
| EP | 0693293 B1 | 1/1996 |
| EP | 0719571 A2 | 7/1996 |
| EP | 775467 | 5/1997 |
| EP | 0853957 B1 | 7/1998 |
| EP | 0867200 A2 | 9/1998 |
| EP | 0982001 | 3/2000 |
| EP | 1051990 A1 | 11/2000 |
| EP | 1070514 A1 | 1/2001 |
| EP | 1402922 A1 | 3/2004 |
| EP | 1428473 | 6/2004 |
| EP | 1541188 A1 | 6/2005 |
| EP | 1618924 A1 | 1/2006 |
| EP | 1759637 | 3/2007 |
| JP | 10137250 A | 5/1998 |
| JP | 2001120561 A | 5/2001 |
| RU | 2177350 C2 | 12/2001 |
| WO | WO 90/05485 | 5/1990 |
| WO | WO 92/10932 | 7/1992 |
| WO | WO 93/09724 | 5/1993 |
| WO | 9520241 A1 | 7/1995 |
| WO | 9712540 A1 | 4/1997 |
| WO | WO 97/19723 | 6/1997 |
| WO | 9745053 A2 | 12/1997 |
| WO | 9815315 A1 | 4/1998 |
| WO | WO 98/16903 | 4/1998 |
| WO | WO 99/11325 | 3/1999 |
| WO | 9934869 A1 | 7/1999 |
| WO | WO 99/33515 | 7/1999 |
| WO | WO 99/42163 | 8/1999 |
| WO | WO 00/51484 | 9/2000 |
| WO | 0114011 A1 | 3/2001 |
| WO | 0143826 A1 | 6/2001 |
| WO | 0158346 A1 | 8/2001 |
| WO | 0209599 A2 | 2/2002 |
| WO | 02069862 A1 | 9/2002 |
| WO | WO 03/020114 | 3/2003 |
| WO | 2004043531 A2 | 5/2004 |
| WO | WO 2004/043535 | 5/2004 |
| WO | 2005037363 A2 | 4/2005 |
| WO | 2005039655 A1 | 5/2005 |
| WO | 2005039665 A1 | 5/2005 |
| WO | WO 2005/051197 | 6/2005 |
| WO | 2005067442 A2 | 7/2005 |
| WO | WO 2005/110230 | 11/2005 |
| WO | WO 2005/112767 | 12/2005 |
| WO | WO 2006/055830 | 5/2006 |
| WO | WO 2006/058160 | 6/2006 |
| WO | 2007027831 A1 | 3/2007 |
| WO | 2007143560 A2 | 12/2007 |

(56) References Cited

FOREIGN PATENT DOCUMENTS

| | | |
|---|---|---|
| WO | WO 2008/067557 | 6/2008 |
| WO | WO 2009/079170 | 6/2009 |

OTHER PUBLICATIONS

*SenoRX, Inc.* v. *Hologic, Inc.*; District Court for the District of Delaware, Case No. 1:12-cv-00173-LPS-CJB, Hologic, Inc.'s Answer to Complaint and Counterclaim filed on May 23, 2012.
*SenoRX, Inc.* v. *Hologic, Inc.*; District Court for the District of Delaware, Case No. 1:12-cv-00173-LPS-CJB, SenoRX's Answer to Counterclaim filed on Jun. 18, 2012.
*SenoRX, Inc.* v. *Hologic, Inc.*; District Court for the District of Delaware, Case No. 1:12-cv-00173-LPS-CJB, Joint Claim Construction Chart, filed Nov. 16, 2012.
Cuttino, L. W., et al., "CT-Guided Multi-Catheter Insertion Technique for Partial Breast Brachytherapy: Reliable Target Coverage and Dose Homogeneity", Brachytherapy 4, 2005, pp. 10-17, Elsevier.
Glasgow, G. P., et al. "Remote Afterloading Technology", AAPM Report No. 41, 1993, pp. i-vi and 1-107, American Institute of Physics, Inc.
Hoshino, T., "Brain Tumor Research Center", Abstracts of the 11th Conference on Brain Tumor Research and Therapy, Journal of Neuro-Oncology 28, 1996, pp. 31-113.
Tanderup, et al, "Multi-Channel Intracavitary Vaginal Brachytherapy Using Three-Dimensional Optimization of Source Geometry", Radiation & Oncology Journal of the European Society for Therapeutic Radiology and Oncology, 2004, pp. 81-85, Radiotherapy and Oncology 70 (2004), Elsevier Ireland Ltd.
Devic, et al., "Advantages of Inflatable Multichannel Endorectal Applicator in the Neo-Adjuvant Treatment of Patients With Locally Advanced Rectal Cancer With HDR Brachytherapy", Journal of Applied Clinical Medical Physics, Spring 2005, pp. 44-49, vol. 6, No. 2.
Symon, et al. "Individual Fraction Optimization vs. First Fraction Optimization for Multichannel Applicator Vaginal Cuff High-Dose-Rate Brachytherapy", pp. 211-215, Brachytherapy 5 (2006), Elsevier.
Friedman, M, et al., "A New Technic for the Radium Treatment of Carcinoma of the Bladder", Presented at the Thirty-fourth Annual Meeting of the Radiological Society of North America, Dec. 5-10, 1948, pp. 342-362.
Walton, R. J., "Therapeutic Uses of Radioactive Isotopes in the Royal Cancer Hospital", The British Journal of Radiology, 1950, pp. 559-599, William Heinemann, Publisher.
Low-Beer, B. V. A., "Radioisotope Therapy", "The Clinical Use of Radioactive Isotopes" 1950, pp. 284-349, Charles C. Thomas, Publisher, Springfield, Illinois, U.S.A., See pp. 343-349.
Low-Beer, B. V. A., "The Therapeutic Use of Radioactive Isotopes", "Practical Therapeutics", Dec. 1954, pp. 69-87, vol. X, No. 6.
Muller, J. H., "Radiotherapy of Bladder Cancer by Means of Rubber Balloons Filled In Situ With solutions of a Radioactive Isotope (Co60)", Cancer, A Journal of the American Cancer Society, Jul.-Aug. 1955, pp. 1035-1043, vol. 8, No. 4, J. B. Lippincott Company, Philidelphia.
Friedman, M, et al., "Irradiation of Carcinoma of the Bladder by a Central Intracavitary Radium or Cobalt 60 Source (The Walter Reed Technique)", Presented at the Annual Meeting of the American Radium Society, 1955, pp. 6-31.
Hewitt, C. B., et al., "Update on Intracavitary Radiation in The Treatment of Bladder Tumors", The Journal of Urology; Official Journal of The American Urological Association, Inc., 1981, pp. 323-325, vol. 126 September, The Williams & Wilkins Co.
Hieshima, G. B., et al. "A Detachable Balloon for Therapeutic Transcatheter Occlusions 1", Technical Notes, Jan. 1981, pp. 227-228, vol. 138.
Russel, A. H., et al, "Intracavitary Irradiation for Carcinoma of the Urinary Bladder: Rationale, Technique, and Preliminary Results", Int. J. Radiation Oncology. Phys,. 1984, pp. 215-219, vol. 10, Pergamon Press Ltd.

Yin, W., "Brachtherapy of Carcinoma of the Esophagus in China, 1970-1974 and 1982-1984", Brachytherapy HDR and LDR, May 4-6, 1989, pp. 52-56.
Kaufman, N., "Remote Afterloading Intraluminal Brachytherapy in The Treatment of Rectal, Rectosigmoid, and Anal Cancer: A Feasibility Study", International Journal of Radiation Oncology, Biology, Physics, Sep. 1989, pp. 663-668, vol. 17, Issue 3, Pergamon Press plc.
Wolf, C. D., et al., "A Unique Nasopharynx Brachytherapy Technique", Official Journal of the American Association of Medical Dosimetrists, 1990, pp. 133-136, vol. 15, Issue No. 3., Pergamon Press.
Fowler, J. F., "Brief Summary of Radiobiological Principles in Fractionated Radiotherapy", Seminars in Radiation Oncology, Jan. 1992, pp. 16-21, vol. 2, No. 1, W. B. Saunders Company.
Nag, S, "Modern Techniques of Radiation Therapy for Endometrial Cancer", Clinical Obstetrics and Gynecology, Sep. 1996, pp. 728-744, vol. 39, No. 3, Lippincott-Raven Publishers.
Pernot, M., "Combined Surgery and Brachytherapy in the Treatment of Some Cancers of the Bladder (Partial Cystectomy and Interstitial Iridium-192)", Radiotherapy & Oncology, 1996, pp. 115-120, Elsevier Science Ireland Ltd.
Micheletti, E., et al., "High-Dose-Rate Brachytherapy for Poor-Prognosis, High-Grade Glioma: (Phase II) Preliminary Results", Tumori, 1996, pp. 339-344.
Nag, S., et al., "Perineal Template Interstitial Barchytherapy Salvage for Recurrent Endometrial Adenocarcinoma Metastatic to the Vagina", Necologic Oncology 66, 1997, pp. 16-19, Article No. GO974722, Academic Press.
Nag, S., et al., "Remote Controlled High Dose Rate Brachytherapy", Critical Reviews in Oncology/Hematology 22, 1996, pp. 127-150, Elsevier Science Ireland Ltd.
Sylvester, J., et al., "Interstitial Implantation Techniques in Prostate Cancer" Journal of Surgical Oncology 1997; 66: 65-75, Wiley-Liss, Inc.
Tan, L. T., et al., Radical Radiotherapy for Carcinoma of the Uterine Cervix Using External Beam Radiotherapy and a Single Line Source Brachytherapy Technique: The Clatterbridge Technique, The British Journal of Radiology, 70, date Dec. 1997, pp. 1252-1258.
Kuettel, M. R., et al., "Treatment of Female Urethral Carcinoma in Medically Inoperable Patients Using External Beam Irradiation and High Dose Rate Intracavitary Brachytherapy" The Journal of Urology, May 1997, pp. 1669-1671, vol. 157, The American Urological Association, Inc.
Slevin, N. J., et al., "Intracavitary Radiotherapy Boosting for Nasopharynx Cancer" The British Journal of Radiology, 70, Apr. 1997, pp. 412-414.
Sneed, P., K., et al., Interstitial Brachytherapy Procedures for Brain Tumors, Seminars in Surgical Oncology 1997; 13: 157-166, Wiley-Liss, Inc.
Dempsey, J. F., et al., "Dosimetric Properties of a Novel Brachytherapy Balloon Applicator for the Treatment of Malignant Brain-Tumor Resection-Cavity Margins" Int. J. Radiation Oncology Biol. Phys., May 1998, pp. 421-429, vol. 42, No. 2, Elsevier.
Kolotas, C., et al., "CT Guided Interstitial High Dose Rate Brachytherapy for Recurrent Malignant Gliomas", The British Journal of Radiology, 72, (1999), pp. 805-808.
Demanes, D, J., et al., "The Use and Advantages of a Multichannel Vaginal Cylinder in High-Dose-Rate Brachytherapy", Int. J. Radiation Oncology Biol. Phys., (1999), pp. 211-219, vol. 44, No. 1, Elsevier Science Inc.
Debicki, M. P., et al., "Localized Current Field Hyperthermia in Carcinoma of the Cervix: 3-D Computer Simulation of SAR Distribution", International Journal of Hyperthermia, 1999, pp. 427-440, vol. 15, No. 5.
Garipagaoglu, M, et al., "Geometric and Dosimetric Variations of ICRU Bladder and Rectum Reference Points in Vaginal Cuff Brachytherapy Using Ovoids", Int. J. Radiation Oncology Biol. Phys . . . 2004, pp. 1607-1615, Elsevier Inc.
Bowsher, W. G., et al., "Update on Urology-Prostate Cancer, 4-Treatment of Local Disease", European Journal of Surgical Oncology, 1995 pp. 679-682, vol. 21, No. 6.

(56) References Cited

OTHER PUBLICATIONS

Voung, T, et al., "High-Dose-Rate Endorectal Brachytherapy in the Treatment of Loacally Advanced Rectal Carcinoma: Technical Aspects", Brachytherapy 4, 2005, pp. 230-235, Elsevier.
Harada, T, et al., "Transcystoscopic Intracavitary irradiation for Carcinoma of the Bladder: Technique and Preliminary Clinical Results", The Journal of Urology, Oct. 1987, pp. 771-774, vol. 138, No. 4, The Williams & Wilkins Co.
Hall, J. W., et al., "Histologic Changes in Squamous-Cell Carcinoma of the Mouth and Oropharynx Produced by Fractionated External Roentgen Irradiation", Radiological Society of North America, 1948, pp. 318-350, 50/3/MAR.
Hine, G. J., et al., "Isodose Measurements of Linear Radium Sources in Air and Water by Means of an Automatic Isodose Recorder",The American Journal of Roentgenology and Radium Therapy, 1950, pp. 989-998, vol. 64, No. 6, The Societies.
Walton, R. J., et al., Radioactive Solution (24Na and 82 Br) in the Treatment of Carcinoma of the Bladder:, British Medical Bulletin, 1952, pp. 158-165, Medical Dept., The British Council.
Marshall V. F., et al., "Current Clinical Problems Regarding Bladder Tumors", Symposium on Bladder Tumors, 1956, pp. 543-550, 9/3/May-Jun., J. B. Lippincott Co, Etc.
Hewitt, C. B., et al., "Intracavitary Radiation in the Treatment of Bladder Tumors", The Journal of Urology, vol. 107, Apr. 1972, pp. 603-606, The Williams & Wilkins Co.
Rotman, M., et al., "The Intracavitary Applicator in Relation to Complications of Pelvic Radiation—The Ernst System", Int. J. Radiation Oncology Biol. Phys., 1978, pp. 951-956, vol. 4, Pergamon Press Inc.
Nag, S., et al., "The Future of High Dose Rate Brachytherapy", High Dose Rate Brachytherapy: A Textbook, 1994, pp. 447-453, Futura Publishing Company, Inc. , Armonk, New York 10504.
Wang, C. C., "Carcinoma of the Nasopharynx", Radiation Therapy of Head and Neck Neoplasms, 1997, pp. 257-280, Chapter 10, Wiley-Liss, Inc.
Gaspar, L. E., et al., "Esophageal Brachytherapy", Principles and Practice of Brachytherapy, 1997, pp. 305-321, Futrua Publishing Company, Inc., Armouk, New York.
Vicini, F. A., et al, "Dose-Volume Analysis for Quality Assurance of Interstitial Brachytherapy for Breast Cancer", Int. J. Radiation Oncology Biol. Phys., vol. 45, 1999, pp. 803-810, Elsevier Science Inc.
Akagi, Y, et al., "Optimum Fractionation for High-Dose-Rate Endoesophageal Brachytherapy Following External Irradiation of Early State Esophageal Cancer", Int. J. Radiation Oncology Biol. Phys., vol. 43, 1999, pp. 525-530, Elsevier Science, Inc.
XP007904995:retrieved from the internet: URL: http://www2.dupont.com/Teflon_industrial/en_US/assets/downloads/h88800.pdf; retrieved on Jun. 19, 2008, by Authorized Officer in International Application PCT/US2008/003364.
Lewis, J, et al., "Intracranial Brachytherapy Using a High Dose Rate Microselectron", Northern Centre for Cancer Treatment, Dept. of Neurosciences, Regional Medical Physics Department, Newcastle General Hospital, Newcastle Upon Tyne, UK, Radiation and Oncology, vol. 39, Supplement 1, May 1996, pp. 45-45(1).
International Search Report for PCT/US2008/003364 mailed Aug. 27, 2008.
Written Opinion of the International Searching Authority for PCT/US2008/003364 dated Sep. 15, 2009.
International Preliminary Report on Patentability for PCT/US2008/003364 issued Aug. 3, 2010.
International Search Report for PCT/US2008/003217 mailed Aug. 12, 2008.
Written Opinion of the International Searching Authority for PCT/US2008/003217 dated Sep. 12, 2009.
International Preliminary Report on Patentability for PCT/US2008/003217 dated Mar. 21, 2011.
International Search Report for PCT/US03/33775 mailed Jun. 21, 2004.
International Preliminary Report on Patentability for PCT/US03/33775 dated Oct. 10, 2007.
International Search Report for PCT/US2006/044067 mailed Dec. 18, 2007.
Written Opinion of the International Searching Authority for PCT/US2006/044067 dated Jan. 11, 2009.
International Preliminary Report on Patentability for PCT/US2006/044067 dated Oct. 2, 2009.
International Search Report for PCT/US2006/043891 mailed Sep. 25, 2007.
Written Opinion of the International Searching Authority for PCT/US2006/043891 dated May 18, 2008.
International Preliminary Report on Patentability for PCT/US2006/043891 dated Jan. 12, 2009.
Office Action dated Feb. 1, 2013 in U.S. Appl. No. 13/571,495.
Office Action dated Mar. 13, 2013 in U.S. Appl. No. 13/649,668.
Paul V. Harper, "Some Therapeutic Applications of Radioisotopes", Journal of the Mississippi State Medical Association, Oct. 1966, vol. VII, pp. 526-533.
"Variable shield for radiation-therapy source wire and centering catheter", Research disclosure, Mason Publications, Hampshire, GB, vol. 438, No. 48, Oct. 2000, XP007126916.
Gregory K. Edmundson, et al., "Dosimetric Characteristics of the Mammosite RTS, a New Breast Brachytherapy Applicator", Int. J. Radiation Oncology Biol. Phys, vol. 52, No. 4, pp. 1132-1139, 2002.
Melvin A. Astrahan, PhD et al., "Optimization of Mammosite therapy", Int. J. Radiation Oncology Biol. Phys, vol. 58, No. 1, pp. 220-232, 2004.
Philip H. Gutin, et al., "A coaxial catheter system for afterloading radioactive sources for the interstitial irradiation of brain tumors", J. Neurosur, vol. 56, pp. 734-735, 1982.
R.D. Ashpole et al., "A New Technique of Brachytherapy for Malignant Gliomas with Caesium-137; A New Method Utilizing a Remote Afterloading system", Clinical Oncology, (1990).
Abstracts of the 11th International Conference on Brain tumor Research and Therapy Oct. 31-Nov. 3, 1995, Silverado Country Club and Resort, Napa, California, Journal of Neuro-Oncology 28:72, 1996.
Johannesen, T.B. et al, "Intracavity Fractioned Balloon Brachytherapy in Glioblastoma", Acta Neurochir (Wien) (1999) 141: 127-133.
Xu, Z., et al., "Calculation of Dose Distribution Near an Innovative Concentric Balloon Catheter for Endovascular Brachytherapy", Cardiovascular Radiation Medicine 2, 2000, pp. 26-31, Elsevier Science Inc.
Stubbs, J. B., et al., "Preclinical Evaluation of a Novel Device for Delivering Brachytherapy to the Margins of Resected Brain Tumor Cavities", J. Neurosurg 96, Feb. 2002, pp. 335-343, vol. 96.
Das, R. K., et al., "3D-CT-Based High-Dose-Rate Breast Brachytherapy Implants: Treatment Planning and Quality Assurance", Int. J. Radiation Oncology Biol. Phys. 2004, pp. 1224-1228, vol. 59, No. 4, Elsevier Inc.
"Essentials for life: Senographe Essential Full-Field Digital Mammography system", GE Health-care Brochure, MM-0132-05.06-EN-US, 2006, 12 pgs.
"Filtered Back Projection," (NYGREN) published May 8, 2007; URL:http://web.archive.org/web/19991010131715/http://www.owlnet.rice.edu/-.about.e1ec539/Projects97/cult/node2.html, 2 pgs.
"Lorad Selenia" Document B-BI-SEO US/Intl (May 2006), copyright Hologic 2006, 12 pgs.
Chan, Heang-Ping et al., "ROC study of the effect of stereoscopic imaging on assessment of breast lesions", Medica Physics, vol. 32, No. 4, Apr. 2005, 7 pgs.
Cole, Elodia, et al., "The Effects of Gray Scale Image Processing on Digital Mammography Interpretation Performance", Academic Radiology, vol. 12, No. 5, pp. 585-595, May 2005.
Digital Clinical Reports, Tomosynthesis, GE Brochure 98-5493, Nov. 1998, 8 pgs.
Federica Pediconi et al., "Color-coded automated signal intensity-curve for detection and characterization of breast lesions: Preliminary evaluation of a new software for MR-based breast imaging", International Congress Series 1281 (2005) 1081-1086.

(56) References Cited

OTHER PUBLICATIONS

Kita et al., "Correspondence between different view breast X-rays using simulation of breast deformation", Proceedings 1998 IEE Computer Society Conference on Computer Vision and Pattern Recognition, Santa Barbara, CA, Jun. 23-25, 1998, pp. 700-707.

Mammographic Accreditation Phantom, http://www.cirsinc.com/pdfs/015cp.pdf, (2006), 2 pgs.

Nath, Ph.D. et al., "Development of an 241 Am Applicator for Intracavitary Irradiation of Gynecologic Cancers", I.J. Radiation Oncology Biol. Phys., May 1988, vol. 14, p. 969-978.

Senographe 700 & 800T (GE); 2-page download on Jun. 22, 2006 from www.gehealthcare.com/inen/rad/whe/products/mswh800t.html.; Figures 1-7 on 4 sheets re lateral shift compression paddle, 2 pgs.

Smith, A., "Fundamentals of Breast Tomosynthesis", White Paper, Hologic Inc., WP-00007, Jun. 2008, 8 pgs.

Wheeler, F.W. et al. (2006), "Micro-Calcification Detection in Digital Tomosynthesis Mammography", Proceedings of SPIE, Conf-Physics of Semiconductor Devices, Dec. 11, 2001 to Dec. 15, 2001, Delhi, SPIE, US, vol. 6144, Feb. 13, 2006, 12 pgs.

Wu, Tao et al., "Tomographic mammography using a limited number of low-dose cone-beam images", Medical Physics, AIP, Melville, NY, vol. 30, No. 3, Mar. 1, 2003, pp. 365-380.

Office Action dated Jun. 11, 2013 in U.S. Appl. No. 13/861,195 issued by the United States Patent and Trademark Office.†

† cited by third party

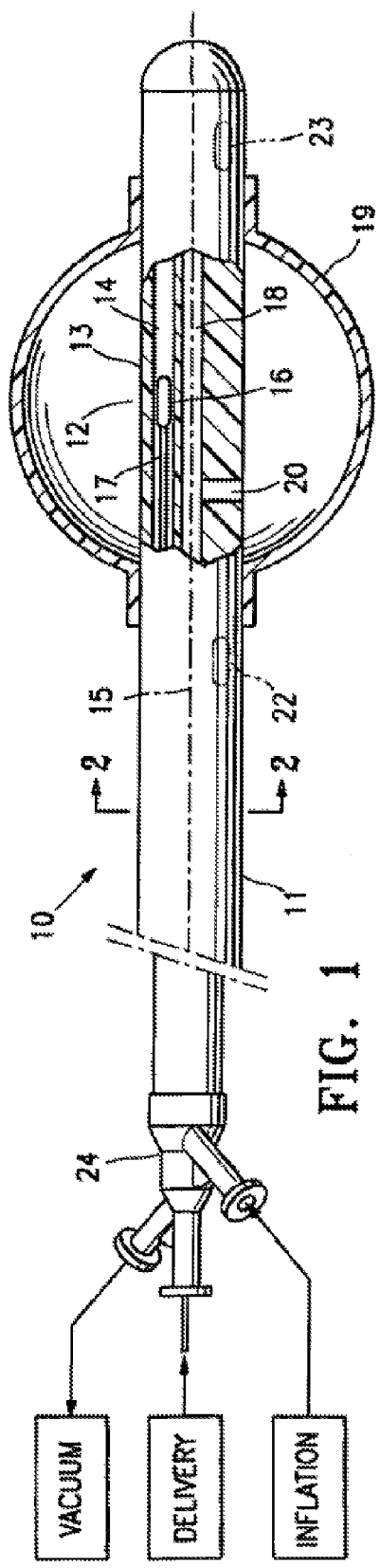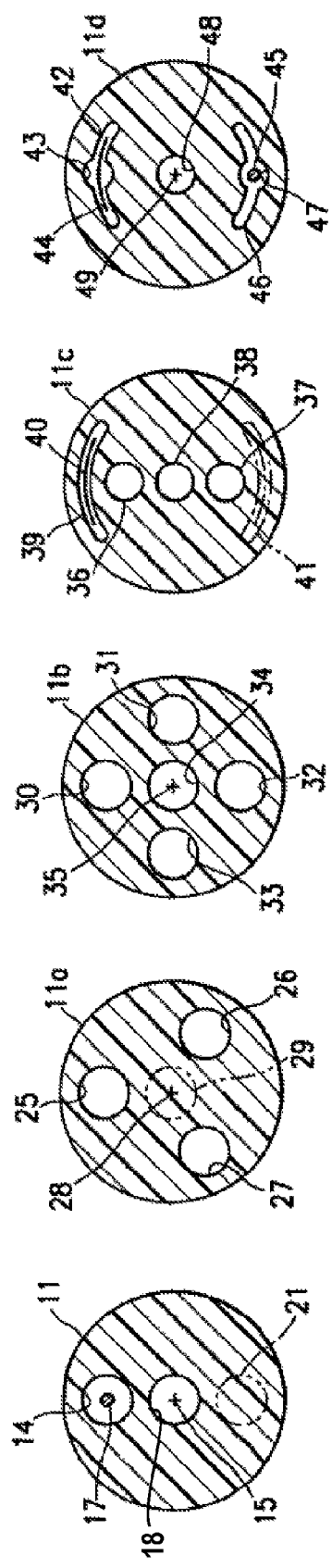

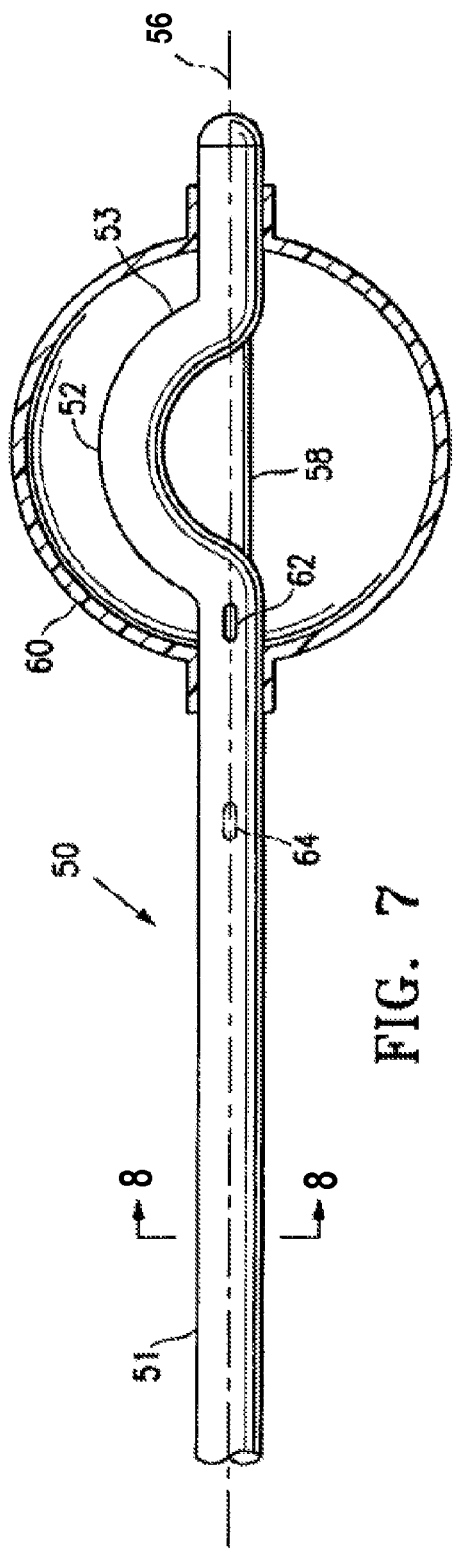
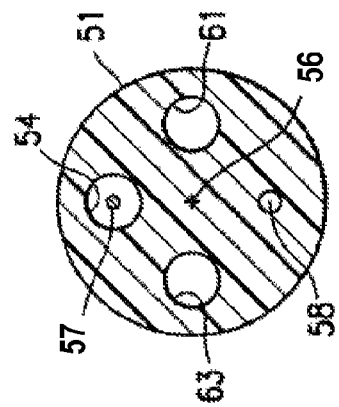
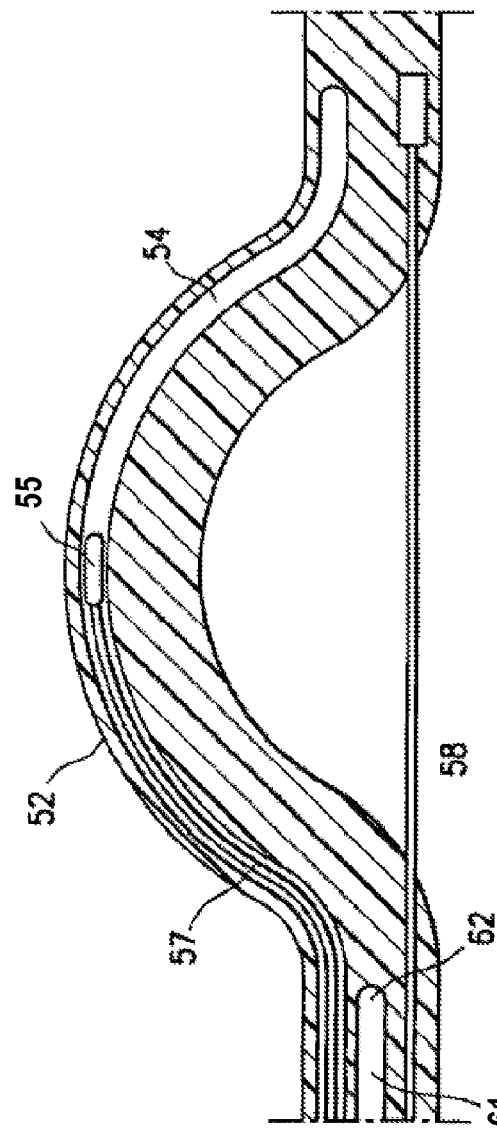

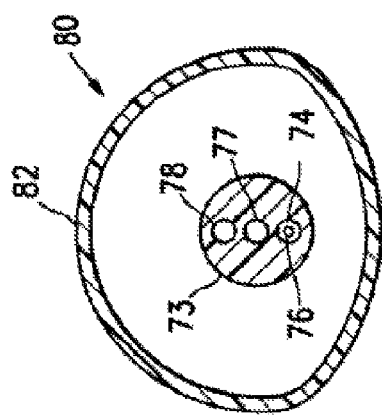
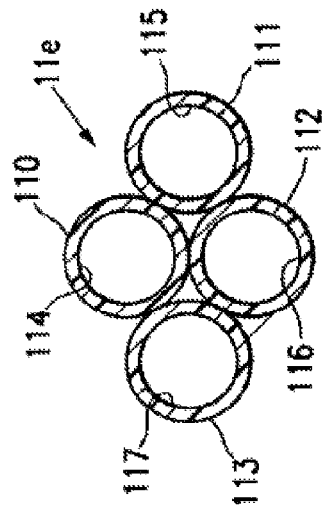
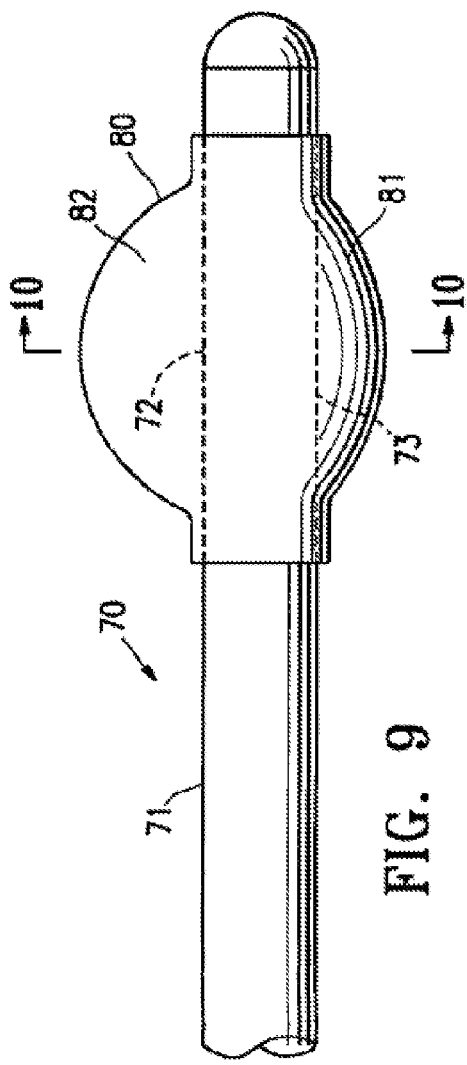
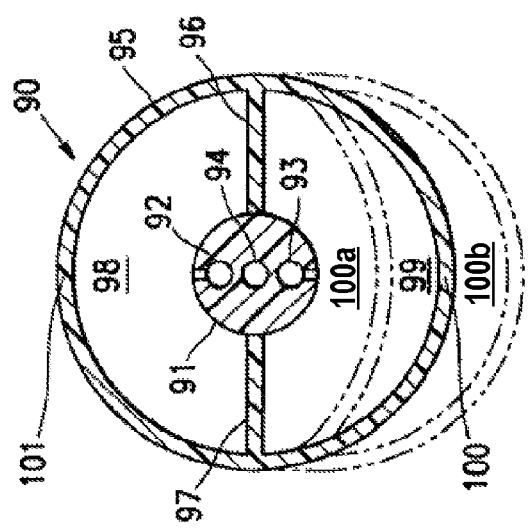

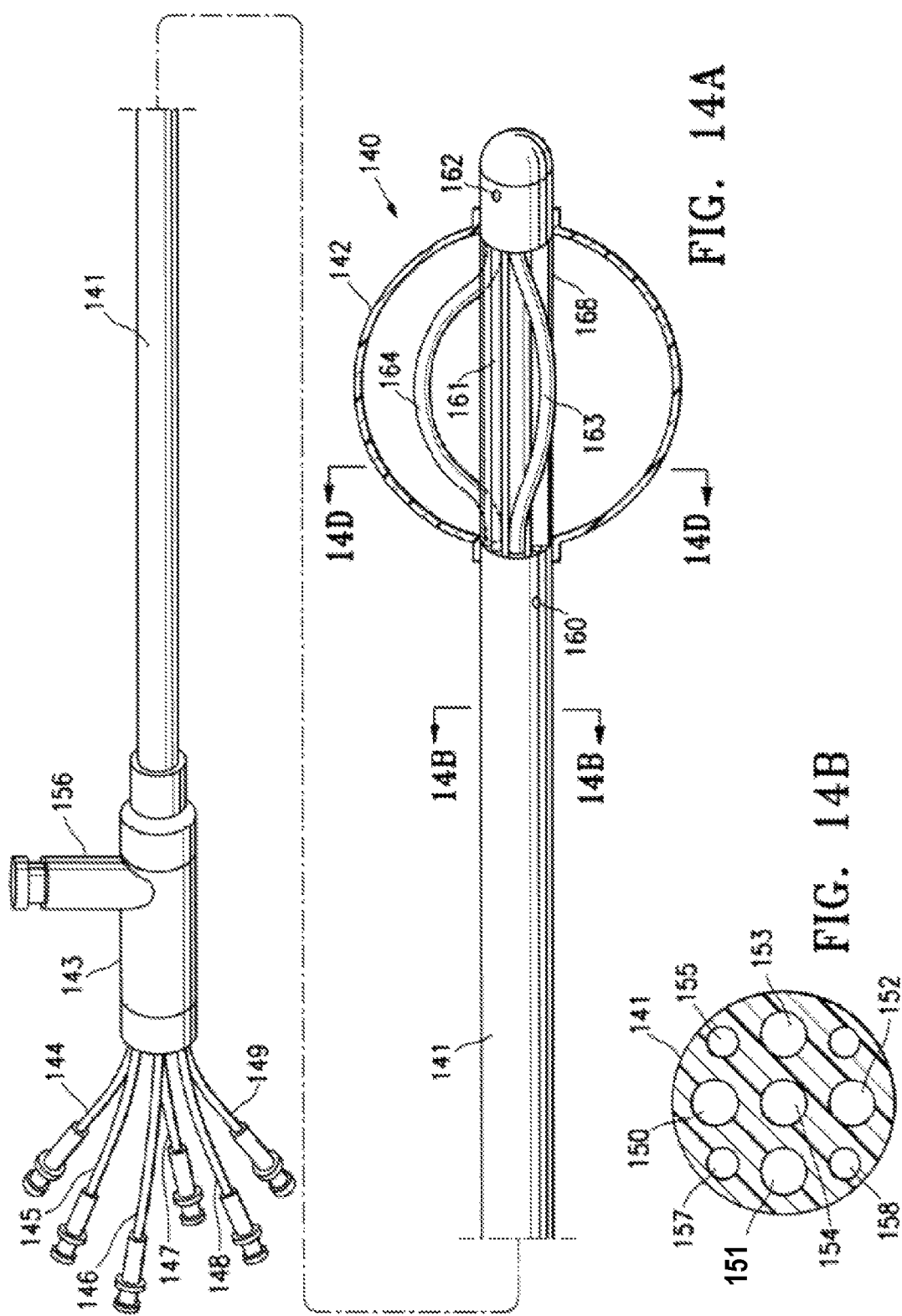

BRACHYTHERAPY DEVICE FOR FACILITATING ASYMMETRICAL IRRADIATION OF A BODY CAVITY

RELATED APPLICATIONS

This application is a continuation of application Ser. No. 11/593,784, filed Nov. 6, 2006 now U.S. Pat. No. 8,079,946, which is a continuation-in-part of application Ser. No. 11/283,236, filed Nov. 18, 2005, now U.S. Pat. No. 7,413, 539, and which also is related to provisional application Ser. No. 60/819,919 filed on Jul. 11, 2006, entitled Radiation Device For A Body Cavity, all from which priority is claimed and which are incorporated herein by reference in their entireties.

FIELD OF THE INVENTION

This invention relates generally to the fields of medical treatment devices and methods. In particular, the invention relates to devices and methods for treating tissue surrounding a body cavity, such as a site from which cancerous, pre-cancerous, or other tissue has been removed.

BACKGROUND OF THE INVENTION

In diagnosing and treating certain medical conditions, it is often desirable to perform a biopsy, in which a specimen or sample of tissue is removed for pathological examination, tests and analysis. A biopsy typically results in a biopsy cavity occupying the space formerly occupied by the tissue that was removed. As is known, obtaining a tissue sample by biopsy and the subsequent examination are typically employed in the diagnosis of cancers and other malignant tumors, or to confirm that a suspected lesion or tumor is not malignant. Treatment of cancers identified by biopsy may include subsequent removal of tissue surrounding the biopsy site, leaving an enlarged cavity in the patient's body. Cancerous tissue is often treated by application of radiation, by chemotherapy, or by thermal treatment (e.g., local heating, cryogenic therapy, and other treatments to heat, cool, or freeze tissue).

Cancer treatment may be directed to a natural cavity, or to a cavity in a patient's body from which tissue has been removed, typically following removal of cancerous tissue during a biopsy or surgical procedure. For example, U.S. Pat. No. 6,923,754 to Lubock and U.S. patent application Ser. No. 10/849,410 to Lubock, the disclosures of which are all hereby incorporated by reference in their entireties, describe devices for implantation into a cavity resulting from the removal of cancerous tissue which can be used to deliver cancer treatments to surrounding tissue. One form of radiation treatment used to treat cancer near a body cavity remaining following removal of tissue is "brachytherapy" in which a source of radiation is placed near to the site to be treated.

Lubock above describes implantable devices for treating tissue surrounding a cavity left by surgical removal of cancerous or other tissue that includes an inflatable balloon constructed for placement in the cavity. Such devices may be used to apply one or more of radiation therapy, chemotherapy, and thermal therapy to the tissue surrounding the cavity from which the tissue was removed. The delivery lumen of the device may receive a solid or a liquid radiation source. Radiation treatment is applied to tissue adjacent the balloon of the device by placing radioactive material such as radioactive "seeds" in a delivery lumen. Such treatments may be repeated if desired.

For example, a "MammoSite® Radiation Therapy System" (MammoSite® RTS, Proxima Therapeutics, Inc., Alpharetta, Ga. 30005 USA) includes a balloon catheter with a radiation source that can be placed within a tumor resection cavity in a breast after a lumpectomy. It can deliver a prescribed dose of radiation from inside the tumor resection cavity to the tissue surrounding the original tumor. The radiation source is typically a solid radiation source; however, a liquid radiation source may also be used with a balloon catheter placed within a body cavity (e.g., Lotrex®, Proxima Therapeutics, Inc.). A radiation source such as a miniature or micro-miniature x-ray tube may also be used (e.g. U.S. Pat. No. 6,319,188). The x-ray tubes are small, flexible and are believed to be maneuverable enough to reach the desired treatment location within a patient's body. The radiation source is to be removed following each treatment session, or remains in place as long as the balloon remains within the body cavity. Inflatable treatment delivery devices and systems, such as the MammoSite® RTS and similar devices and systems (e.g., GliaSite® RTS (Proxima Therapeutics, Inc.)), are useful to treat cancer in tissue adjacent a body cavity.

However, radiation, chemotherapy, thermal treatment, and other cancer treatments often have deleterious effects on healthy tissue in addition to the desired effects on cancerous tissue. In such treatments, care must be taken to direct the maximum treatment effects to diseased tissue while minimizing its delivery or effects on healthy tissue. For example, radiation treatment may be most effective when only the portion of tissue requiring treatment receives the radiation and where surrounding healthy tissue is unaffected. Tissue cavities typically are not uniform or regular in their sizes and shapes, so that differences in dosages applied to different regions of surrounding tissue, including "hot spots" and regions of relatively low dosage, often result from radiation treatment.

A treatment delivery device for treating tissue adjacent a body cavity has been disclosed in U.S. Pat. No. 6,923,754. This device applies a partial-vacuum or suction to bring tissue towards a radiation source and allows for uniform application of radiation to tissue surrounding a body cavity. An advantage of the present invention is that it allows for the protection of healthy tissue within that body cavity and provides a seal in the passageway leading to the body cavity while treating the desired tissue.

SUMMARY OF THE INVENTION

This invention is generally directed to treating a patient's body cavity or other intracorporeal site (hereinafter collectively referred to as a body cavity) and devices and methods for such treatments. The invention is particularly suitable for treating tissue adjacent to a body cavity formed by the removal of tissue such as in a biopsy or lumpectomy.

More specifically, a device embodying features of the invention has a distal portion with a treatment location which is configured to be asymmetrically deployed within the body cavity so as to be closer to a first portion of tissue surrounding the cavity than a second portion of tissue surrounding the cavity opposite the first tissue portion. The treatment location of the distal portion which includes or is configured to receive a radiation source such as a brachytherapy seed or other irradiating agent for irradiating the first portion of tissue surrounding the body cavity more intensely that the second portion of tissue surrounding the body cavity opposed to the first portion of tissue due to the radiation source being closer to the first tissue portion than to the second tissue portion.

In one embodiment the treatment location having a radiation source is offset or capable of being offset within the body cavity so that tissue of the first portion of the cavity receives more intense radiation treatment than the tissue of the second portion.

This invention is generally directed to treating a patient's body cavity or other intracorporeal site and devices and methods for such treatments. The invention is particularly suitable for treating tissue adjacent to a body cavity such as a cavity formed by the removal of tissue.

More specifically, a device embodying features of the invention has a distal portion with a treatment location which is configured to be asymmetrically deployed within the body cavity and which is configured to receive or which includes a brachytherapy or other irradiating agent for treating tissue surrounding the cavity or other site.

In one embodiment the treatment location having a radiation source is offset or capable of being offset from the central location within the body cavity so that tissue of one portion of the cavity receives more intense radiation treatment than the tissue of an opposing portion.

The invention is generally directed to treating a patient's body cavity by irradiation, and devices and methods for such treatments. The invention is particularly suitable for treating tissue adjacent a patient's body cavity, such as that formed by removal of tissue for a biopsy.

More specifically, a device embodying features of the invention includes a treatment location at a distal portion of the device which is configured to receive or which includes a brachytherapy agent, such as a radiation source and which has a centrally located longitudinal axis. The distal portion of the shaft with the treatment location is deployable within the body cavity so as to provide asymmetrical treatment such as irradiation thereto to tissue surrounding the cavity and is or is capable of being deployed away from the longitudinal axis and closer to one portion of the cavity than an opposed portion.

In one embodiment the distal portion of the device has at least one delivery lumen which is configured to receive a radiation source and which is off-set or capable of being off-set from a central longitudinal axis so that the radiation source is closer to the tissue of the first portion of the body cavity than the tissue of the second portion of the cavity at an opposing side resulting in greater levels of radiation being received by the first tissue portion of the cavity. In this embodiment the device may also have one or more radiation shielding components that provide further control of the radiation emitted from the radiation source, such as described in application Ser. No. 11/593,952 (now U.S. Pat. No. 7,407,476), entitled Tissue Irradiation With Shielding. Off-setting the lumen in which the radiation source is deployed places the radiation source closer to a first tissue portion surrounding the body cavity to provide greater levels of radiation thereto and further away from the second tissue portion surrounding the body cavity at other locations to reduce the level of radiation thereto. The radiation received by the tissue surrounding the body cavity is a function of inverse of the distance (R) from the radiation source squared ($1/R^2$), so even small changes in the location of the radiation source within a body cavity can make a significant impact on the amount of radiation received by tissue in the body cavity or site. In this embodiment the shaft having the distal portion with the treatment location may be deformed to deflect the radiation lumen to an off set location with respect to the central longitudinal axis. An alternative is to provide an asymmetrical cavity filling member that holds the distal portion of the shaft with the treatment location at a desired position within the cavity or body site to provide asymmetrical irradiation to the tissue surrounding the cavity or site. This maybe accomplished with a cavity filling member that is asymmetrical, is mounted asymmetrically on the shaft or is configured to be inflated to an asymmetrical shape. The cavity filling member may have separate chambers which are independently inflated to different sizes so as to develop an asymmetrical shape that results in an off-set of the radiation source.

In another embodiment the device has an outer sheath with an inner lumen and an inner cannula or catheter which is rotatably disposed within the inner lumen of the outer sheath. The cannula or catheter has an inner lumen which is configured to receive a radiation source. The inner lumen receiving the radiation source is off set from a central longitudinal axis of the catheter or cannula, so that rotation of the cannula or catheter within the inner lumen of the outer sheath will adjust the position of a radiation source within the body cavity or site to provide the desired asymmetrical irradiation dose within the cavity.

The elongated shaft may also have one or more radiation shielding components designed to reduce or minimize damaging irradiation of healthy tissue surrounding the body cavity while treating nearby areas having diseased tissue with radiation emitted from the radiation source. The radiation shielding components include one or more radiation shields disposed about a delivery shaft containing the radiation source. Suitable radiation shielding components are described in application Ser. No. 11/593,952 (now U.S. Pat. No. 7,407,476), entitled Tissue Irradiation With Shielding.

A device embodying features of the invention preferably has an enlarged or enlargeable cavity filling member at the treatment location which at least in part fills the body cavity. Preferably, the cavity filling member is inflatable member such as a balloon. The elongated shaft has an inner inflation lumen for directing inflation fluid to the interior of the cavity filling member for its inflation.

The device may also include an inner lumen configured to be in fluid communication with a proximal vacuum source and one or more vacuum ports preferably proximal and or distal to the cavity filling member such as described in U.S. Pat. No. 6,923,754 and application Ser. No. 10/849,410 filed on May 19, 2004, (now U.S. Pat. No. 6,955,641), both of which are assigned to the present assignee. Application of a vacuum within the inner lumen aspirates fluid in the cavity through one or more vacuum ports and the vacuum within the body cavity pulls tissue defining the cavity onto the exterior of the cavity filling member deployed within the cavity. The application of a vacuum may also be employed to aspirate fluids from the cavity or site.

A method for treating a body cavity or other intracorporeal site of a patient includes delivering a treatment agent such as a radiation source to a body cavity to treat the desired tissue while minimizing damaging irradiation of healthy tissues. More specifically, a method for treating a body cavity or intracorporeal site includes providing a device having an elongate shaft with a proximal end, a distal end, and a treatment location in a distal portion of the shaft. The method further includes providing a radiation source configured to be deposited in the treatment location and a radiation shielding component partially encircling the treatment location which is configured to control at least in part the emission of radiation emitted from the treatment location. The device is advanced within the patient until the treatment location of the device is deployed within the body cavity or site and the radiation source is positioned within the treatment location.

The radiation shielding component is positioned to shield portions of the body cavity from radiation emitted from the radiation source.

A patient's skin is susceptible to damage from radiation delivered by isotopes (e.g. seeds) or x-ray catheters in a lumen of a radiation balloon catheter if the radiation source is to close to the skin. Generally, radiation treatments using a radiation balloon catheter is usually not performed on patients where the body cavity (e.g. from a lumpectomy) is less than 5 mm, sometimes less than 7 mm from the patient's skin. Additionally, over inflation of the balloon can thin and stretch the skin. The application of a vacuum to the body cavity can help by pulling the tissue to the balloon and increased cavity to skin surface distances would result. However, in some instances it would still be too thin to treat. The number of potential patient's which are suitable candidates for treatments with the present device is significantly increased due to reducing the potential for skin tissue damage.

Placing patterns of radiation absorbing materials on the surface or within the wall of the balloon would aid in shielding the skin or in other cases, sensitive organs (e.g., heart, lung, ribs, etc.) from unnecessary radiation. Examples include—Mylar with aluminum, balloon coatings with gold, lead, titanium barium and barium sulfate or silver ions incorporated within the balloon wall.

The surface (inside or outside) of the balloon or within the balloon wall may be provided with indicator marks for location or orientation detection during the procedures. For example, dots or lines to help place balloon in appropriate position under CT, x-ray or fluoroscopy. The indicator marks may be radiopaque. Alternatively, or additionally, ultrasound indicators or MRI and direct visual indicators could be incorporated. The indicator marks may extend along the catheter shaft to help with placement of the catheter device during the treatment procedure and the orientation of the off set lumen and shield.

In other embodiments having features of the invention, the radiation shield may be secured to a control rod or band within the catheter device so that the location of the shield may be adjusted. Alternatively, the radiation shield may be secured within or onto the catheter device.

These and other advantages of the present invention are described in more detail in the following written description and the accompanying exemplary drawings.

BRIEF DESCRIPTION OF THE DRAWINGS

FIG. 1 is a schematic view, partially in section, of a brachytherapy device embodying features of the invention including a cavity filling member.

FIG. 2 is a transverse cross sectional view of the device shown in FIG. 1 taken along lines 2-2 which illustrates the device with two inner lumens.

FIG. 3 is a transverse cross sectional view of an alternative device similar to the device shown in FIG. 1 having three lumens.

FIG. 4 is a transverse cross sectional view of an alternative device similar to the device shown in FIG. 1 having 5 lumens.

FIG. 5 is a transverse cross-sectional view of an alternative device having three lumens having circular transverse cross-sections and a pair of opposed arcuate inner lumens for radiation shielding component.

FIG. 6 is a transverse cross-sectional view of a device similar to that shown in FIG. 1 which has a plurality of arcuate lumens with enlarged central portions which allow for the deployment of a radiation shield or a radiation source within the lumens.

FIG. 7 is an elevational view, partially in section, of a distal portion of an alternative design for a brachytherapy device wherein the shaft within the cavity filing member is deformed to place the radiation source closer to one side of the cavity filling member than an opposed site.

FIG. 7A is an enlarged longitudinal cross-section of the deformed shaft within the cavity filling member.

FIG. 8 is a transverse cross-sectional view of the device shown in FIG. 7 taken along the lines 8-8.

FIG. 9 is an elevational view of a distal portion of an alternative design for a brachytherapy device wherein the cavity filling member is asymmetric, or inflated to an asymmetric configuration to place the radiation source closer to one side of the body cavity or site.

FIG. 10 is a transverse cross-sectional view of the brachytherapy device shown in FIG. 9 taken along the lines 10-10.

FIG. 11 is a transverse cross-sectional view similar to that shown in FIG. 10 in which the interior of the cavity filling member is separated into two chambers by a membrane so that each chamber may be inflated, e.g. to different sizes.

FIG. 12 illustrates a shaft formed of a plurality of elongated elements with at least one of the elongated elements having an inner lumen configured to receive a radiation source.

FIG. 14A is a perspective view, partially in section, of an alternative device which has a plurality of radially extending tubular members for delivery of radiation sources.

FIG. 14B is a transverse cross-sectional view of the device shown in FIG. 14A taken along the lines 14B-14B.

DETAILED DESCRIPTION OF THE INVENTION

Figures 13A, 13B:
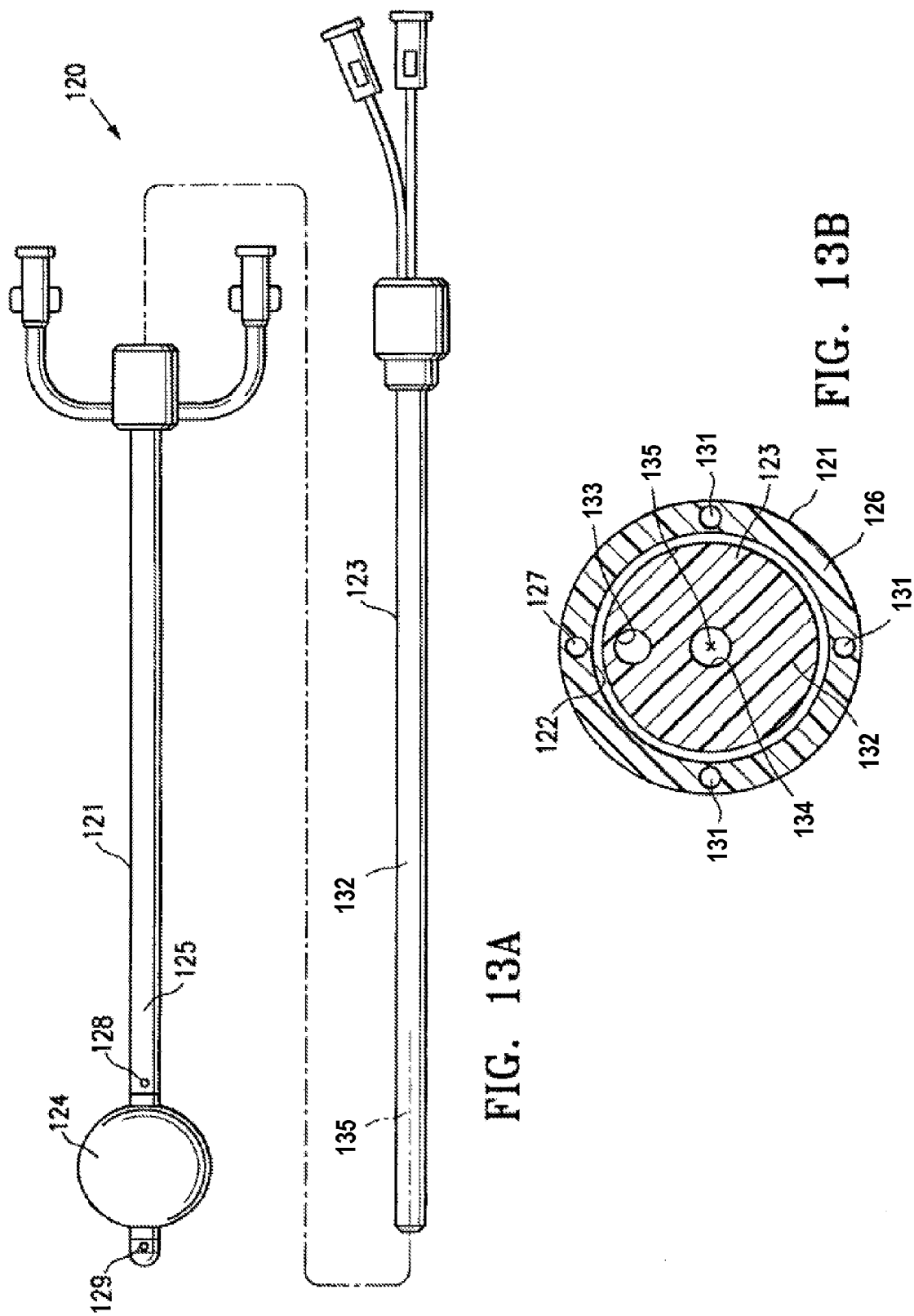
FIGS. 13A-B illustrate another embodiment having features of the invention which has an outer catheter with a cavity filling member and an inner catheter with an inner lumen which is off set or off settable from a longitudinal axis.
Figure 14D:
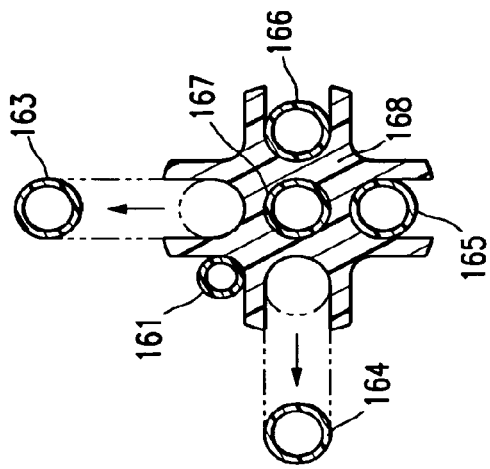
FIG. 14D is a transverse cross-sectional view of the device shown in FIG. 14A taken along the lines 14D-14D.
Figure 14C:
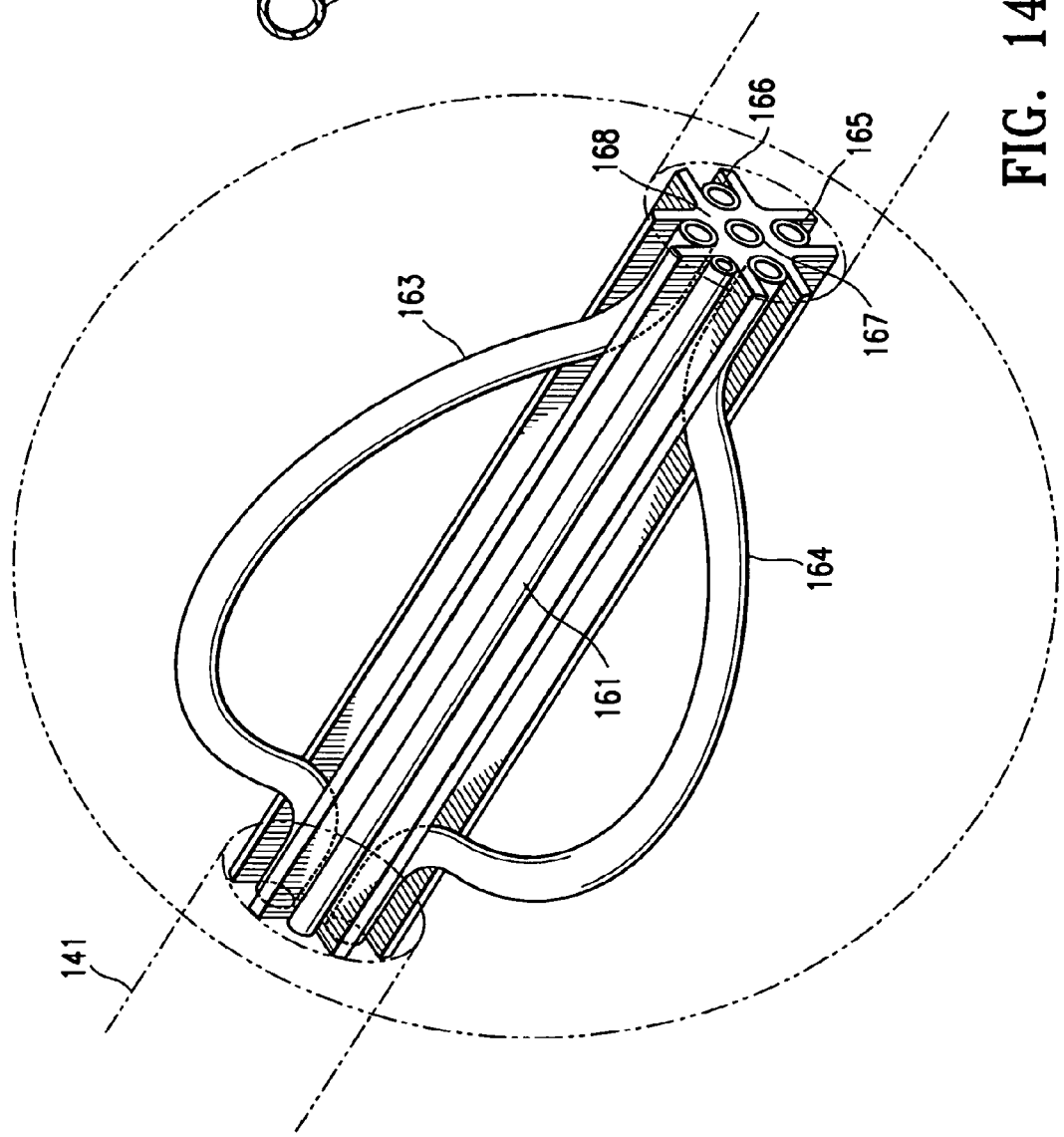
FIG. 14C is a perspective view of a compartmented support member and tubular members which extend through an inflatable member.

The present invention is directed to devices and methods for treatment of a patient's body cavity, particularly to deliver asymmetrical radiation into a biopsy cavity or into a cavity left after removal of tissue from the patient's body. Other body sites may also be treated.

FIGS. 1 and 2 illustrate a brachytherapy device 10 embodying features of the invention which has an elongated shaft 11 with a treatment location 12 in a distal portion 13 of the elongated shaft 11. The elongated shaft 11 has a first lumen 14 which is off set from central longitudinal axis 15 and which is configured to receive a radiation source 16. The radiation source 16 is disposed at the distal end of pusher rod 17 to facilitate deployment within the treatment location 12. The elongated shaft 11 also has a second lumen 18 for delivery of inflation fluid to the interior of the cavity filling member 19 through inflation port 20. The elongated shaft 11 may also have a third lumen 21 shown in phantom to provide a vacuum to a desired location such as vacuum ports 22 and 23 also shown in phantom which are proximal and/or distal to the cavity filling member 19 as described in U.S. Pat. No. 6,923, 641 (assigned to the present assignee). The third lumen may also be utilized as an off-set lumen to receive a radiation source in the event the first lumen 14 is not in a desired location when the distal end of the device is placed in the patient and the physician does not wish to rotate the device 10. The proximal end of the elongated shaft 11 has a multi-arm adapter 24 for delivery of a vacuum, inflation fluid and radiation source as shown. The device 10 may also have one or more radiation shielding components (not shown) to further reduce radiation to tissue which is not to be treated. Suitable radiation shielding components are described in application Ser. No. 11/593,952 (now U.S. Pat. No. 7,407,476), entitled Tissue Irradiation With Shielding which has been assigned to the present assignee.

A body cavity within a patient may be treated with the device 10 by inserting the distal shaft portion 13 into the desired body cavity with the off-set first lumen 14 configured to receive the radiation source 16 being closer to a first tissue portion surrounding the cavity to be treated and farther away from a second tissue portion surrounding the cavity which needs to be protected. A radiation source 16 is advanced within the first lumen 14 until the radiation source is properly positioned within the treatment location 12 (or prepositioned therein). Inflation fluid is delivered to the interior of the cavity filling member 19 so as to at least partially fill the body cavity. A vacuum may be generated about the cavity filling member 19 through vacuum ports 22 and 23 to conform the tissue surrounding the cavity to the exterior of the cavity filling member. The radiation source 16 is maintained at the treatment location 12 for a prescribe period of time, usually less than 30 minutes and typically a few (5-10) minutes. At the end of the treatment time the radiation source may be removed from device 10 or the entire device may be withdrawn from the patient. Preferably, the device is left in place so that further radiation treatments may be performed.

FIG. 3 illustrates an elongated shaft 11a of an alternative brachytherapy device which has three off-set lumens 25, 26 and 27 that are equally disposed about the longitudinal axis 28. The first off-set lumen 25 may be used as the radiation delivery lumen such as described above for first lumen 14. The second and third off-set lumens 26 and 27 may be utilized for delivery of inflation fluid to the interior of a cavity filling member (not shown) or for delivery of a vacuum to vacuum ports (not shown) proximal or distal to the cavity filling member as described above. Additionally, a centrally located fourth lumen 29 (shown in phantom) may be provided as an alternative lumen for radiation delivery in the event an off-set location is not needed. The fourth lumen may also be employed as an inflation or vacuum lumen as described above, leaving one of the off-set lumens 26 and 27 to deliver a radiation source in the event the first off-set lumen is not in a desirable location when the device is deployed within the patient's body cavity.

FIG. 4 illustrates an elongated shaft 11b of another alternative design of device 10 which has four off set lumens 30-33, one central lumen 34 which is axially aligned with longitudinal axis 35. The off set lumens 30-33 and central lumen 34 may be utilized as in the prior embodiments. This embodiment provides additional alternative lumens for delivery of a radiation source (not shown) as described above.

FIG. 5 illustrates yet another elongated shaft 11c of an alternative design which has two off set lumens 36 and 37 and a central lumen 38 which have circular transverse cross-sections as shown. The off set and central lumens 36, 37 and 38 may be utilized as described above. Additionally, at least one arcuate lumen 39 may be provided to facilitate placement of a radiation shield 40 as described in application Ser. No. 11/593,952 (now U.S. Pat. No. 7,407,476) entitled Tissue Irradiation With Shielding. A second arcuate lumen 41 at an opposed position within the shaft 11c (shown in phantom) for delivery of a radiation shield in the event the device is not placed in a desired orientation and the physician does not want to rotate the device.

FIG. 6 depicts another elongated shaft 11d for an alternative brachytherapy device 10 which has a first arcuate lumen 42 with an enlarged central portion 43. This first arcuate lumen 42 is design to slidably receive a radiation shielding member 44 and the enlarged central portion 43 is designed to slidably receive a radiation source 45 such as shown in second arcuate lumen 46 with enlarged central portion 47. A central lumen 48 is axially disposed about the longitudinal axis 49 and may be utilized for delivery of inflation fluid or a vacuum to the distal portion of the device. This design allows for the flexibility of placing either a radiation source or a radiation shielding member on either side of the device. The central lumen 48 may alternatively be positioned off-set within the shaft 11d. Other off-set lumens may be provided as described above with respect to the other embodiments.

FIGS. 7, 7A and 8 depict an alternative brachytherapy device 50 which has an elongated shaft 51 with a treatment location 52 in a distal portion 53 thereof. The shaft 51 is deformable within the treatment location 52. The elongated shaft 51 has a first lumen 54 which is configured to receive a radiation source 55 to position a radiation source off set from the longitudinal axis 56. The radiation source 55 has a standard pusher rod 57 to facilitate placement of the radiation source at the treatment location 52 within the first lumen 54. The distal shaft portion 53 is deformed, i.e. radially deflected, by pull-wire 58 so that the treatment location 52 is off-set or further off set from the longitudinal axis 56. The distal end of the pull-wire 58 has an enlarged hub which secures the distal end of the pull-wire within the shaft. The deformation of the distal shaft portion 53 places the radiation source 55 closer to one side of the cavity filling member 60 thereby reducing the radiation to tissue of the opposing side of the cavity. While only one pull-wire 58 is illustrated, multiple pull-wires may be employed about the longitudinal axis 56 to facilitate deformation of the distal shaft portion 53 in multiple directions. Other mechanical structures, may be provided to radially deflect the distal shaft portion 53 away from longitudinal axis 56. Off-set lumen 61 leads to inflation port 62 for directing inflation fluid to the interior of the cavity filling member 60. Off-set lumen 63 leads to vacuum port 64 (shown in phantom) proximal to the cavity filling member 60 to generate a vacuum within the body cavity to aspirate fluids and/or to conform surrounding tissue of the body cavity to the exterior of the cavity filling member 60.

FIGS. 9 and 10 illustrate another brachytherapy device 70 embodying features of the invention. The device 70 has an elongated shaft 71, a treatment location 72 in distal shaft portion 73, a first lumen 74 configured to receive radiation source 76, a second lumen 77 and a third lumen 78 and an asymmetrical cavity filling member 80. The first lumen 74 is closest to the smaller side 81 of the cavity filling member 80 so that radiation through the smaller side 81 of the cavity filling member 80 to adjacent tissue is greater than the radiation through the larger side 82 to adjacent tissue. The larger side 82 of the cavity filling member 80 is placed next to tissue in which the radiation dose is to be minimized, whereas the smaller side 81 is positioned adjacent to tissue which is to receive a higher dose of radiation. The second and third lumens 77 and 78 may be utilized for vacuum and inflation fluid as discussed above with respect to other embodiments.

FIG. 11 shows an alternative brachytherapy device 90 which has an elongated shaft 91 with three inner lumens. Off set lumens 92 and 93 and centrally disposed lumen 94. The first off set lumen 92 is for receiving a radiation source as previously described. The second off set lumen 93 may be for vacuum, inflation fluid or as an alternative lumen for a radiation source. The central lumen 94 may be employed for vacuum, inflation fluid or alternatively a radiation source. The device 90 has a cavity filling member 95 which has inner membranes 96 and 97 which separate the interior of the cavity filling member into separate chambers 98 and 99. Each chamber has separate sources (lumens) for inflation fluid so that one side 100 of the cavity filling member 95 may be inflated to one or more different sizes than an adjacent side 101. As shown in phantom, the side 100 may be inflated to a smaller size 100a or a larger size 100b. Adjusting the sizes controls the location of the radiation source within a lumen. With a smaller size 100a, the tissue to be treated adjacent to side 100 receives a higher radiation dose than tissue adjacent to side 101 which should be protected and given a smaller radiation dose. Alternatively, when chamber 98 is inflated so that side 100 is of a larger size, the tissue adjacent to side 100 will receive more radiation.

FIG. 12 depicts an elongate shaft 11e of an alternative device which comprises a plurality of elongated tubular elements 110, 111, 112 and 113. At least one of the elongated elements 110 has a first inner lumen 114 configured for receiving a radiation source such as described above for the other embodiments. The other elongated elements may also have inner lumens 115-117 for delivery of inflation fluid to a cavity filling member (not shown) on a distal portion of the shaft, for delivery of a vacuum to a vacuum port proximal or distal to the cavity filling member or an additional lumen for receiving a radiation source. The plurality of elements 110-113 may be bundled together by one or more outer straps or bands or by an outer sheath or by a suitable adhesive. The plurality of elongated elements of the shaft may be twisted or braided together. Tubular element 110 (as well as 111-113) may be radially deflected as depicted in FIG. 7 to position the first inner lumen closer to the first tissue portion surrounding the body cavity than the second tissue portion.

FIGS. 13A-B illustrate a brachytherapy device 120 which has an outer catheter 121 with an inner lumen 122 and an inner catheter 123 which is configured to be rotatably disposed within the inner lumen 122. The outer catheter 121 has an inflatable cavity filling member 124 on a distal portion 125 of shaft 126. The wall of shaft 126 has at least one lumen 127 for directing inflation fluid to the interior of the cavity filling member 124. The outer catheter 121 also has vacuum ports 128 and 129 proximal and distal to the cavity filling member 124. The wall of shaft 126 has at least one lumen 131 which is in fluid communication with a vacuum port and preferably two lumens. The inner catheter 123 has an elongated shaft 132 with an off-set lumen 133 and may also have a central lumen 134 configured for receiving a radiation source to provide an asymmetrical radiation dose about longitudinal axis 135.

FIGS. 14A-14D illustrate an alternative device 140 which has an elongated shaft 141, a cavity filling balloon 142 on the distal portion of the shaft and an adapter 143 on the proximal end of shaft 141. A plurality of tubes 144-148 extend into the adapter 143 and are in fluid communication with lumens 150-154 respectively within the shaft 141 which are configured to receive radiation sources (not shown) such as those previously described. The device 140 also has an inflation tube 149 which is in fluid communication with lumen 155 that extends to and is in fluid communication with the interior of the balloon 142 to facilitate delivery of inflation fluid thereto. The adapter 143 has a vacuum arm 156 that is in fluid communication with lumens 157 and 158. Lumen 158 is in fluid communication with proximal vacuum port 160 and lumen 157 is in fluid communication with tubular member 161 which in turn is in fluid communication with distal vacuum port 162. Radiation delivery tubes 163-167 are in fluid communication with lumens 150-154. Radiation tube 163 and 164 are radially extended within the interior of balloon 142 in order to be closer to a first tissue portion surrounding a body cavity as previously described. While tubes 163 and 164 are shown as being radially extended within the balloon 142, one radiation delivery tube or more than two radiation delivery tubes may radially extend within the balloon 142 depending upon the need for a particular treatment.

A compartmented support element 168 extends between the proximal and distal ends of the balloon 142. The support element 168 shown has nine compartments 170-174 which are designed to receive tubular radiation delivery members 163-167 respectively. The device 140 may be assembled with the radial extension of radiation delivery tubes 144 and 145 fixed as shown or they may be slidable within the catheter shaft 141 so that the radial extension of these delivery tube be effected during the procedure. The radial extension of the radiation delivery tubes will not usually extend to contact the interior surface of the inflated balloon 142.

The radiation delivery tubes 144-148, which extend into the adapter 143, may extend through the lumens in shaft 141 and may form tubes 163-167 which are received by the support member 163.

All of the radiation delivery tubes which extend through the interior of the balloon 142 would not necessarily be used in a procedure and in fact would probable not be used. However, they would be available for use by the physician if needed, e.g. when the catheter is not in a desired position and rotation of the catheter is not appropriate or desirable. The shaft 141 is shown as a solid shaft having a plurality of passageways. However, the shaft 141 may be made more flexible by utilizing a plurality of tubes which are bundled together form the shaft as shown in FIG. 12.

The radiation source 16 for the brachytherapy device 10 can include a solid or liquid radiation source. Suitable liquid radiation sources include, for example, a liquid containing a radioactive iodine isotope (e.g., $I^{125}$ or $I^{131}$), a slurry of a solid isotope, for example, $^{198}$Au or $^{169}$Yb, or a gel containing a radioactive isotope. Liquid radiation sources are commercially available (e.g., Lotrex®, Proxima Therapeutics, Inc., Alpharetta, Ga.). The radiation source 16 preferably includes brachytherapy seeds or other solid radiation sources used in radiation therapy, for example, a radioactive microsphere available from 3M Company of St. Paul, Minn. Microminiature x-ray source may also be utilized. The radiation source 16 may be either preloaded into the device 10 at the time of manufacture or may be loaded into the device 10 before or after placement into a body cavity or other site of a patient. Solid radionuclides suitable for use with a device 10 embodying features of the present invention are currently generally available as brachytherapy radiation sources (e.g., I-Plant™ Med-Tec, Orange City, Iowa.). Radiation may also be delivered by a device such as the x-ray tube of U.S. Pat. No. 6,319,188. The x-ray tubes are small, flexible and are believed to be capable of being maneuverable enough to reach the desired location within a patient's body.

The brachytherapy device 10 having features of the invention can be provided with a lubricious coating, such as a hydrophilic material. The lubricious coating preferably is applied to the elongate shaft 12 or to the cavity filling member, if one is present, or both to reduce sticking and friction during insertion of a device 10. Hydrophilic coatings such as those provided by AST, Surmodics, TUA Systems, Hydromer, or STS Biopolymers are suitable.

A device 10 having features of the invention may also include an antimicrobial coating that covers all or a portion of the device 10 to minimize the risk of introducing of an infection during extended treatments. The antimicrobial coating preferably is comprised of silver ions impregnated into a hydrophilic carrier. Alternatively the silver ions are implanted onto the surface of the device 10 by ion beam deposition. The antimicrobial coating preferably is comprised of an antiseptic or disinfectant such as chlorhexadiene, benzyl chloride or other suitable biocompatible antimicrobial materials impregnated into hydrophilic coatings. Antimicrobial coatings such as those provided by Spire, AST, Algon, Surfacine, Ion Fusion, or Bacterin International would be suitable. Alternatively a cuff member covered with the antimicrobial coating is provided on the elongated shaft of the delivery device 10 at the point where the device 10 enters the skin.

While particular forms of the invention have been illustrated and described herein, it will be apparent that various modifications and improvements can be made to the invention. Some details of the brachytherapy devices have not been disclosed. To the extent not otherwise disclosed herein, materials and structure may be of conventional design.

Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention be defined by the scope of the appended claims as broadly as the prior art will permit.

Terms such as "element", "member", "component", "device", "means", "portion", "section", "steps" and words of similar import when used herein shall not be construed as invoking the provisions of 35 U.S.C. §112(6) unless the following claims expressly use the terms "means for" or "step for" followed by a particular function without reference to a specific structure or a specific action. All patents and all patent applications referred to above in this application as filed are hereby incorporated by reference in their entirety.

What is claimed is:

1. A brachytherapy device for treating tissue surrounding a body cavity within a patient, comprising:
   a. an elongated shaft having a longitudinal axis and a distal shaft portion, and having a plurality of tubular members that extend along the distal shaft portion, the distal shaft portion being configured to be deployed within the body cavity, the plurality of tubular members being configured to be radially off-set from the longitudinal axis at the distal shaft portion to facilitate asymmetric irradiation of the body cavity when the distal shaft portion is deployed within the body cavity, wherein the plurality of tubular members are configured to selectively and individually expand away from the distal shaft portion; and
   b. an expandable member coupled to the elongated shaft to define an expandable volume around the distal shaft portion, and wherein the expandable member is configured to be spaced apart from plurality of tubular members when the plurality of tubular members are expanded.

2. A brachytherapy device for facilitating asymmetrical irradiation of a body cavity, comprising:
   an elongated shaft having a proximal end, a distal end, and a distal shaft portion proximal to the distal end, the elongated shaft having a centrally located longitudinal axis; and
   an expandable member coupled to the elongated shaft to define an expandable volume at the distal shaft portion, the elongated shaft including:
      a plurality of off-set radiation delivery lumens, each off-set radiation delivery lumen of the plurality of off-set radiation delivery lumens having a respective off-set treatment portion radially off-set from the longitudinal axis within the expandable volume defined by the expandable member, and with each off-set radiation delivery lumen of the plurality of off-set radiation delivery lumens being configured to selectively and individually expand away from the longitudinal axis and receive a radiation source and guide the radiation source into the respective off-set treatment portion, and
      an inflation lumen coupled in fluid communication with the expandable volume defined by the expandable member, the inflation lumen being configured for connection to an inflation fluid source, wherein the expandable member is configured to be spaced apart from the plurality of off-set radiation delivery lumens when the plurality of off-set radiation delivery lumens are expanded.

3. The brachytherapy device of claim 2, wherein each respective off-set radiation delivery lumen is configured to slidably hold the radiation source at a selected dwell position within the respective off-set treatment portion.

4. The brachytherapy device of claim 2, wherein the elongated shaft further includes a central radiation delivery lumen having a central treatment portion located within the expandable volume on the longitudinal axis, with each respective off-set treatment portion being radially off-set from the central treatment portion.

5. The brachytherapy device of claim 4, wherein each respective off-set treatment portion and the central treatment portion extends longitudinally across the expandable volume defined by the expandable member.

6. The brachytherapy device of claim 4, wherein each respective off-set treatment portion and the central treatment portion is located at a respective fixed position relative to the longitudinal axis.

7. The brachytherapy device of claim 4, wherein each of the plurality of off-set radiation delivery lumens, the central radiation delivery lumen, and the inflation lumen has a respective proximal portion that extends proximally from the proximal end of the elongated shaft.

8. The brachytherapy device of claim 7, wherein at least the respective proximal portion of each of the plurality of off-set radiation delivery lumens, the central radiation delivery lumen, and the inflation lumen is flexible to facilitate movement of the respective proximal portion relative to the elongated shaft.

9. The brachytherapy device of claim 4, comprising three off-set treatment portions equally disposed around the central treatment portion.

10. The brachytherapy device of claim 2, comprising multiple off-set treatment portions equally disposed around the longitudinal axis.

11. The brachytherapy device of claim 2, wherein the expandable member is a balloon.

12. A brachytherapy device for facilitating asymmetrical irradiation of a body cavity, comprising:
    an elongated shaft having a proximal end, a distal end, and a distal shaft portion proximal to the distal end; and
    an expandable member coupled to the elongated shaft to define an expandable volume at the distal shaft portion, the elongated shaft including:

a central radiation delivery lumen having a central treatment portion located within the expandable volume, a plurality of off-set radiation delivery lumens, each off-set radiation delivery lumen of the plurality of off-set radiation delivery lumens having a respective off-set treatment portion radially off-set from the central treatment portion within the expandable volume, wherein the plurality of off-set radiation delivery lumens are configured to selectively and individually expand away from the central radiation delivery lumen, the central radiation delivery lumen and each of the plurality of off-set radiation delivery lumens being respectively configured to receive a radiation source and guide the radiation source into the respective treatment portion, and an inflation lumen coupled in fluid communication with the expandable volume defined by the expandable member, wherein the expandable member is configured to be spaced apart from the plurality of off-set radiation delivery lumens when the plurality of off-set radiation delivery lumens are expanded.

13. The brachytherapy device of claim 12, wherein each respective off-set radiation delivery lumen is configured to slidably hold the radiation source at a selected dwell position within the respective off-set treatment portion.

14. The brachytherapy device of claim 12, wherein the central radiation delivery lumen is configured to slidably hold the radiation source at a selected dwell position within the central treatment portion.

15. The brachytherapy device of claim 12, wherein each respective off-set treatment portion and the central treatment portion extends longitudinally across the expandable volume defined by the expandable member.

16. The brachytherapy device of claim 12, wherein each respective off-set treatment portion and the central treatment portion is located at a respective fixed position relative to a central longitudinal axis of the elongated shaft.

17. The brachytherapy device of claim 12, wherein each of the plurality of off-set radiation delivery lumens, the central radiation delivery lumen, and the inflation lumen has a respective proximal portion that extends proximally from the proximal end of the elongated shaft.

18. The brachytherapy device of claim 17, wherein at least the respective proximal portion of each of the plurality of off-set radiation delivery lumens, the central radiation delivery lumen, and the inflation lumen is flexible to facilitate movement of the respective proximal portion relative to the elongated shaft.

19. The brachytherapy device of claim 12, comprising three off-set treatment portions equally disposed around the central treatment portion.

20. The brachytherapy device of claim 12, comprising multiple off-set treatment portions equally disposed around the central treatment portion.

21. The brachytherapy device of claim 1, wherein the expandable member is configured to expand separately from the plurality of tubular members.

22. The brachytherapy device of claim 2, wherein the expandable member is configured to expand separately from the plurality of off-set radiation delivery lumens.

23. The brachytherapy device of claim 12, wherein the expandable member is configured to expand separately from the plurality of off-set radiation delivery lumens.

* * * * *